(12) United States Patent
Ziv et al.

(10) Patent No.: US 11,576,811 B2
(45) Date of Patent: Feb. 14, 2023

(54) THREE DIMENSIONAL DEVICES AND METHODS FOR PROLAPSE ALLEVIATION

(71) Applicant: ConTIPI Medical Ltd., Caesarea (IL)

(72) Inventors: Elan Ziv, Ramat-Gan (IL); Zohar Tyroler, Hod-HaSharon (IL); Elisheva Fabrikant, Herzlia (IL); Tal Caspi, Karkur (IL)

(73) Assignee: ConTIPI Medical Ltd., Caesarea (IL)

( * ) Notice: Subject to any disclaimer, the term of this patent is extended or adjusted under 35 U.S.C. 154(b) by 543 days.

(21) Appl. No.: 15/767,401

(22) PCT Filed: Oct. 13, 2016

(86) PCT No.: PCT/IL2016/051113
§ 371 (c)(1),
(2) Date: Apr. 11, 2018

(87) PCT Pub. No.: WO2017/064713
PCT Pub. Date: Apr. 20, 2017

(65) Prior Publication Data

US 2018/0296388 A1    Oct. 18, 2018

Related U.S. Application Data

(60) Provisional application No. 62/240,572, filed on Oct. 13, 2015.

(51) Int. Cl.
*A61F 6/12*    (2006.01)
*A61F 6/08*    (2006.01)

(52) U.S. Cl.
CPC . *A61F 6/12* (2013.01); *A61F 6/08* (2013.01)

(58) Field of Classification Search
CPC ..... A61F 6/12; A61F 6/08; A61F 6/06; A61B 17/12; A61B 17/12022
USPC ........................................................ 128/834
See application file for complete search history.

(56) References Cited

U.S. PATENT DOCUMENTS

| | | |
|---|---|---|
| 2,398,518 A | 5/1946 | Clark |
| 3,811,423 A | 5/1974 | Dickinson, III et al. |
| 4,246,896 A | 1/1981 | Horne, Jr. et al. |
| 4,677,967 A | 7/1987 | Zartman |
| 4,823,814 A | 4/1989 | Drogendijk et al. |
| 5,224,494 A | 7/1993 | Enhorning |

(Continued)

FOREIGN PATENT DOCUMENTS

| | | |
|---|---|---|
| CN | 2464263 | 12/2001 |
| CN | 101287422 | 10/2008 |

(Continued)

OTHER PUBLICATIONS

Notification of Office Action and Search Report dated Oct. 24, 2019 From the State Intellectual Property Office of the People's Republic of China Re. Application No. 201680072943.2. (9 Pages).

(Continued)

*Primary Examiner* — Rachael E Bredefeld
*Assistant Examiner* — Brant T Bennett

(57) ABSTRACT

A device sized and shaped for alleviating pelvic organ prolapse when inserted into a vagina, comprising: a treatment rendering portion configured to be adjustable between a first, collapsed state and a second, expanded state, where the second expanded state extends substantially in three dimensions.

15 Claims, 22 Drawing Sheets

(56) References Cited

U.S. PATENT DOCUMENTS

| | | | |
|---|---|---|---|
| 5,355,896 | A | 10/1994 | Schulman |
| 5,771,899 | A | 6/1998 | Martelly et al. |
| 5,782,745 | A | 7/1998 | Benderev |
| 5,894,842 | A | 4/1999 | Rabin et al. |
| 6,158,435 | A | 12/2000 | Dorsey |
| 6,216,698 | B1 | 4/2001 | Regula |
| 6,503,190 | B1 | 1/2003 | Ulmsten et al. |
| 6,645,137 | B2 | 11/2003 | Ulmsten et al. |
| 6,808,485 | B2 | 10/2004 | Zunker |
| 7,036,511 | B2 | 5/2006 | Nissenkorn |
| 8,302,608 | B2 | 11/2012 | Harmani |
| 8,651,109 | B2 | 2/2014 | Ziv et al. |
| 2003/0149334 | A1 | 8/2003 | Ulmsten et al. |
| 2008/0009931 | A1 | 1/2008 | Bartning et al. |
| 2008/0167599 | A1 | 7/2008 | Osborn et al. |
| 2009/0203959 | A1 | 8/2009 | Ziv et al. |
| 2009/0266367 | A1* | 10/2009 | Ziv ............. A61F 6/08 128/834 |
| 2009/0283099 | A1 | 11/2009 | Harmanli |
| 2010/0286791 | A1 | 11/2010 | Goldsmith |
| 2013/0025604 | A1 | 1/2013 | Harmanli |
| 2013/0324381 | A1 | 12/2013 | Horsley |
| 2014/0073846 | A1 | 3/2014 | Sinai et al. |
| 2014/0100416 | A1 | 4/2014 | Durling et al. |
| 2014/0158138 | A1 | 6/2014 | Ziv et al. |
| 2014/0261445 | A1 | 9/2014 | Maaskamp et al. |
| 2014/0275744 | A1 | 9/2014 | Rosen et al. |
| 2015/0133725 | A1 | 5/2015 | Ziv et al. |
| 2016/0015500 | A1 | 1/2016 | Ziv et al. |
| 2017/0100278 | A1 | 4/2017 | Ziv et al. |
| 2018/0296387 | A1 | 10/2018 | Ziv et al. |

FOREIGN PATENT DOCUMENTS

| | | |
|---|---|---|
| CN | 101511302 | 8/2009 |
| CN | 102083389 | 6/2011 |
| CN | 202313882 | 7/2012 |
| CN | 102753124 | 10/2012 |
| DE | 169862 | 7/1905 |
| EP | 2276419 | 11/2011 |
| FR | 2843700 | 2/2004 |
| GB | 235218 | 10/1925 |
| GB | 1115727 | 5/1968 |
| JP | 06-133996 | 5/1994 |
| WO | WO 96/01084 | 1/1996 |
| WO | WO 03/047476 | 6/2003 |
| WO | WO 2004/103213 | 12/2004 |
| WO | WO 2008/079271 | 7/2008 |
| WO | WO 2009/130702 | 10/2009 |
| WO | WO 2014/127270 | 8/2014 |
| WO | WO 2014/127295 | 8/2014 |
| WO | WO 2017/064712 | 4/2017 |
| WO | WO 2017/064713 | 4/2017 |
| WO | WO 2017/064714 | 4/2017 |

OTHER PUBLICATIONS

Translation of Notification dated Nov. 17, 2019 From OA of People's Republic of China Re. Application No. 201680072943.2. (9 Pages).
International Preliminary Report on Patentability dated Apr. 26, 2018 From the International Bureau of WIPO Re. Application No. PCT/IL2016/051112. (9 Pages).
International Preliminary Report on Patentability dated Apr. 26, 2018 From the International Bureau of WIPO Re. Application No. PCT/IL2016/051113. (8 Pages).
International Preliminary Report on Patentability dated Apr. 26, 2018 From the International Bureau of WIPO Re. Application No. PCT/IL2016/051114. (8 Pages).
International Search Report and the Written Opinion dated Mar. 2, 2017 From the International Searching Authority Re. Application No. PCT/IL2016/051114. (12 Pages).
International Search Report and the Written Opinion dated Mar. 3, 2017 From the International Searching Authority Re. Application No. PCT/IL2016/051113. (13 Pages).
International Search Report and the Written Opinion dated Apr. 20, 2017 From the International Searching Authority Re. Application No. PCT/IL2016/051112. (15 Pages).
Invitation to Pay Additional Fees dated Feb. 2, 2017 From the International Searching Authority Re. Application No. PCT/IL2016/051112. (2 Pages).
Notification of Office Action and Search Report dated Dec. 18, 2018 From the State Intellectual Property Office of the People's Republic of China Re. Application No. 201680072759.8 and its Translation of Office Action Into English. (6 Pages).
Notification of Office Action and Search Report dated Jun. 11, 2020 From the State Intellectual Property Office of the People's Republic of China Re. Application No. 201680072760.0. (8 Pages).
Notification of Office Action dated Apr. 20, 2020 From the State Intellectual Property Office of the People's Republic of China Re. Application No. 201680072943.2. (4 Pages).
Search Report and Explanationd dated Jun. 9, 2020 From the Servico Publico Federal, Ministerio da Economia, Instituto Nacional da Propriedade Industrial do Brasil Re. BR112018007546-9 and its Summary in English. (5 Pages).
Search Report and Explanationd dated Jun. 9, 2020 From the Servico Publico Federal, Ministerio da Economia, Instituto Nacional da Propriedade Industrial do Brasil Re. BR112018007548-5 and its Summary in English. (5 Pages).
Search Report and Explanations dated Jun. 9, 2020 From the Servico Publico Federal, Ministerio da Economia, Instituto National da Propriedade Industrial do Brasil Re. Application No. BR112018007542-6 and its Summary in English. (5 Pages).
Summary dated May 13, 2020 of Notification of Office Action dated Apr. 20, 2020 From the State Intellectual Property Office of the People's Republic of China Re. Application No. 201680072943.2. (2 Pages).
Official Action dated Jul. 16, 2019 From the US Patent and Trademark Office Re. U.S. Appl. No. 14/881,200. (28 pages).
Supplementary European Search Report and the European Search Opinion dated Jun. 24, 2019 From the European Patent Office Re. Application No. 16855065.5. (8 Pages).
Supplementary Partial European Search Report and the European Search Opinion dated Sep. 9, 2019 From the European Patent Office Re. Application No. 16855066.3. (10 Pages).
Official Action dated Dec. 2, 2019 From the US Patent and Trademark Office Re. U.S. Appl. No. 14/881,200. (17 pages).
Notification of Office Action dated Dec. 25, 2020 From the State Intellectual Property Office of the People's Republic of China Re. Application No. 201680072760.0. and its English Summary (8 Pages).
Official Action dated Jan. 29, 2021 From the US Patent and Trademark Office Re. U.S. Appl. No. 15/767,390. (23 Pages).
Communication Pursuant to Article 94(3) EPC dated Sep. 15, 2021 From the European Patent Office Re. Application No. 16855065.5. (4 Pages).
Official Action dated Sep. 20, 2021 from the US Patent and Trademark Office Re. U.S. Appl. No. 14/881,200. (24 pages).
English Summary dated Aug. 12, 2021 of Notification of Office Action dated May 18, 2021 From the State Intellectual Property Office of the People's Republic of China Re. Application No. 201680072760.0. (2 Pages).
Examination Report Under Sections 12 & 13 of the Patents Act, 1977 and the Patents Rules, 2003 dated Jun. 5, 2021 From the Government of India, Intellectual Property India, Patents, Designs, Trade Marks, Geographical Indications, The Patent Office Re. Application No. 201837017323. (6 Pages).
Final Official Action dated Aug. 4, 2021 from the US Patent and Trademark Office Re. U.S. Appl. No. 15/767,390. (24 pages).
Under Sections 12 & 13 of the Patents Act, 1970 and the Patents Rules, 2003 dated Jun. 5, 2021 From the Government of India, Intellectual Property India, Patents, Designs, Trade Marks, Geographical Indications, The Patent Office Re. Application No. 201837017341. (7 Pages).
Dictonary "Dictionary Definitions Circumference", 2021.

(56) References Cited

OTHER PUBLICATIONS

Communication Pursuant to Article 94(3) EPC dated May 10, 2021 From the European Patent Office Re. Application No. 16855065.5. (5 Pages).
Decision of Rejection dated May 18, 2021 From the State Intellectual Property Office of the People's Republic of China Re. Application No. 201680072760.0. (5 Pages).
Examination Report Under Sections 12 & 13 of the Patents Act, 1970 and the Patents Rules, 2003 dated May 24, 2021 From the Government of India, Intellectual Property India, Patents, Designs, Trade Marks, Geographical Indications, The Patent Office Re. Application No. 201837017313. (5 Pages).
Notification of Decision of Rejection dated Mar. 11, 2021 From the State Intellectual Property Office of the People's Republic of China Re. Application No. 201680072943.2. (6 Pages).
Translation Dated Jun. 8, 2021 of Notification of Decision of Rejection dated Mar. 11, 2021 From the State Intellectual Property Office of the People's Republic of China Re. Application No. 201680072943.2. (10 Pages).
Interview Summary dated Nov. 21, 2021 from US Patent and Trademark Office Re. U.S. Appl. No. 14/881,200. (2 pages).
Notice of Allowance dated Jan. 26, 2022 together with Interview Summary dated Dec. 1, 2021from US Patent and Trademark Office Re. U.S. Appl. No. 15/767,390. (15 pages).

\* cited by examiner

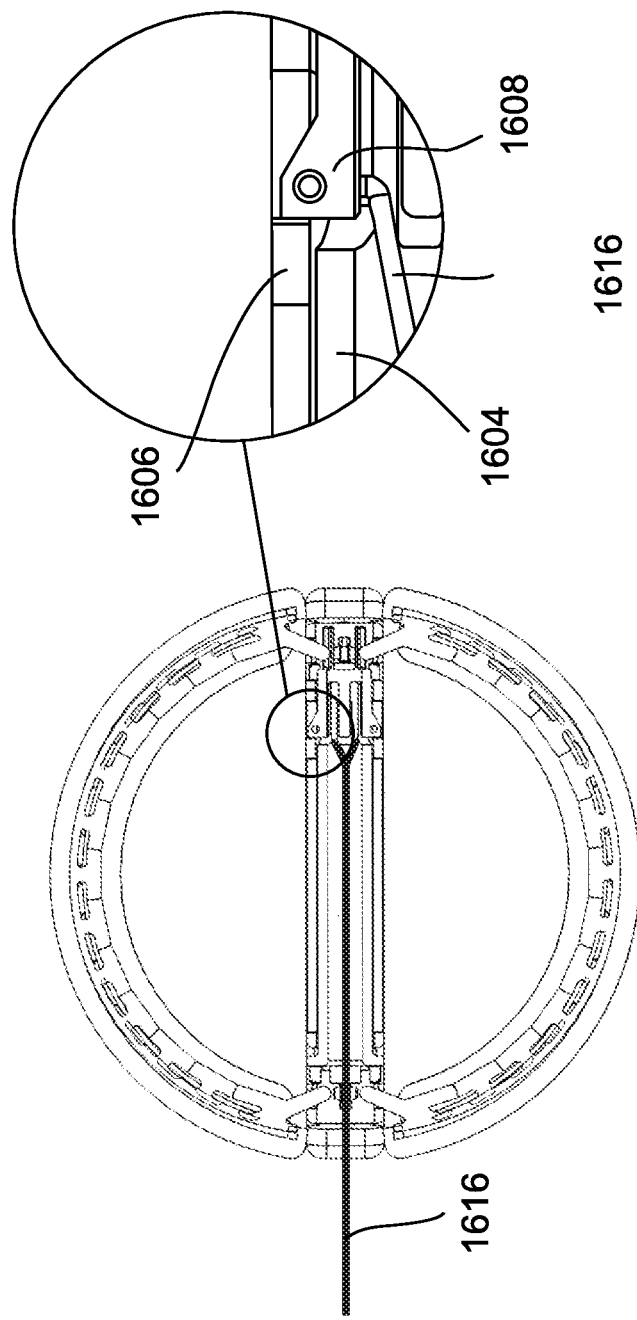

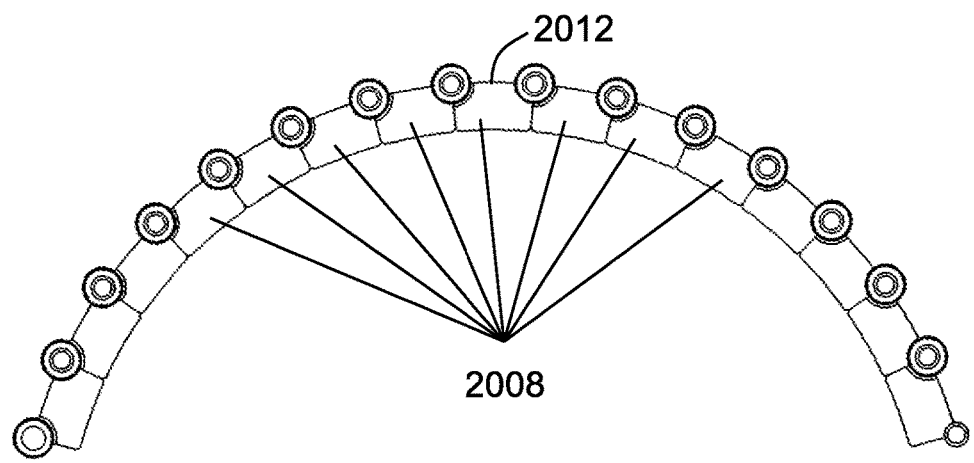
FIG. 22
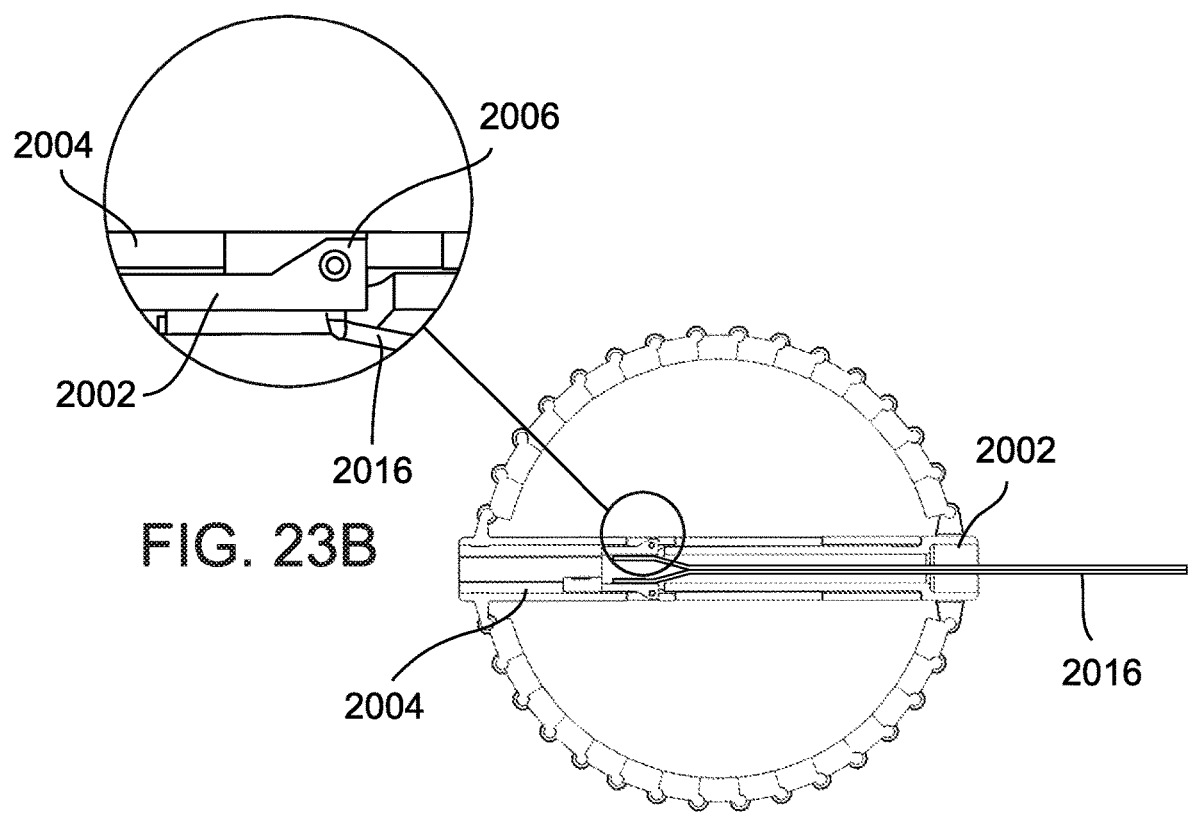
FIG. 23B
FIG. 23A

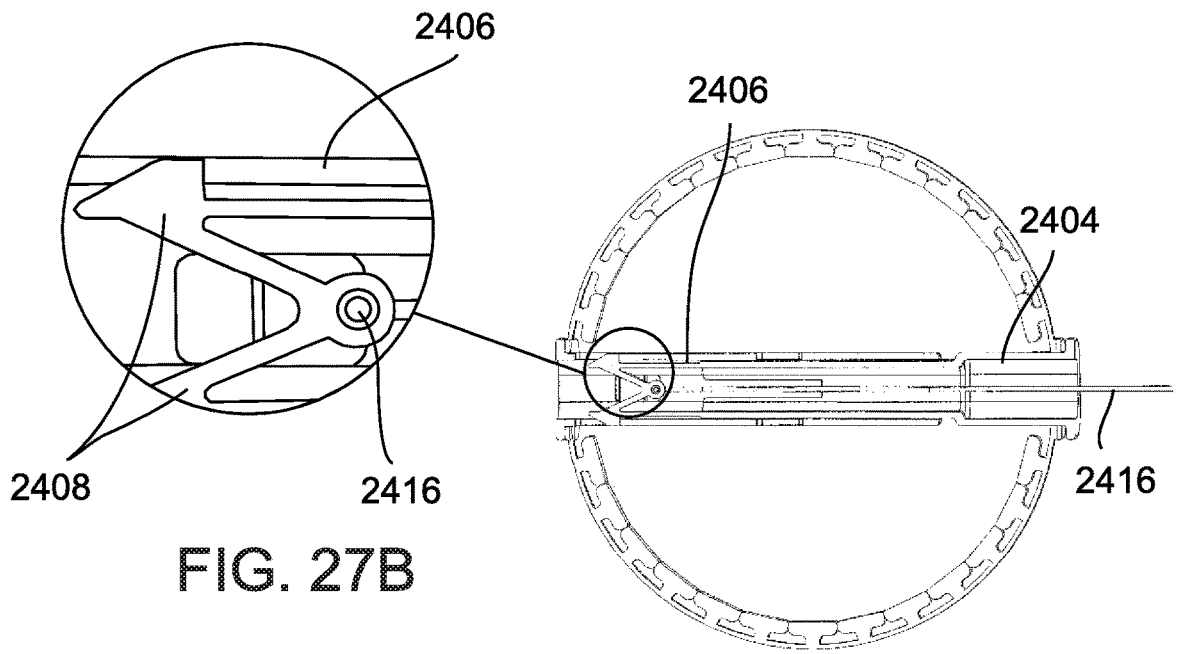
FIG. 27B
FIG. 27A
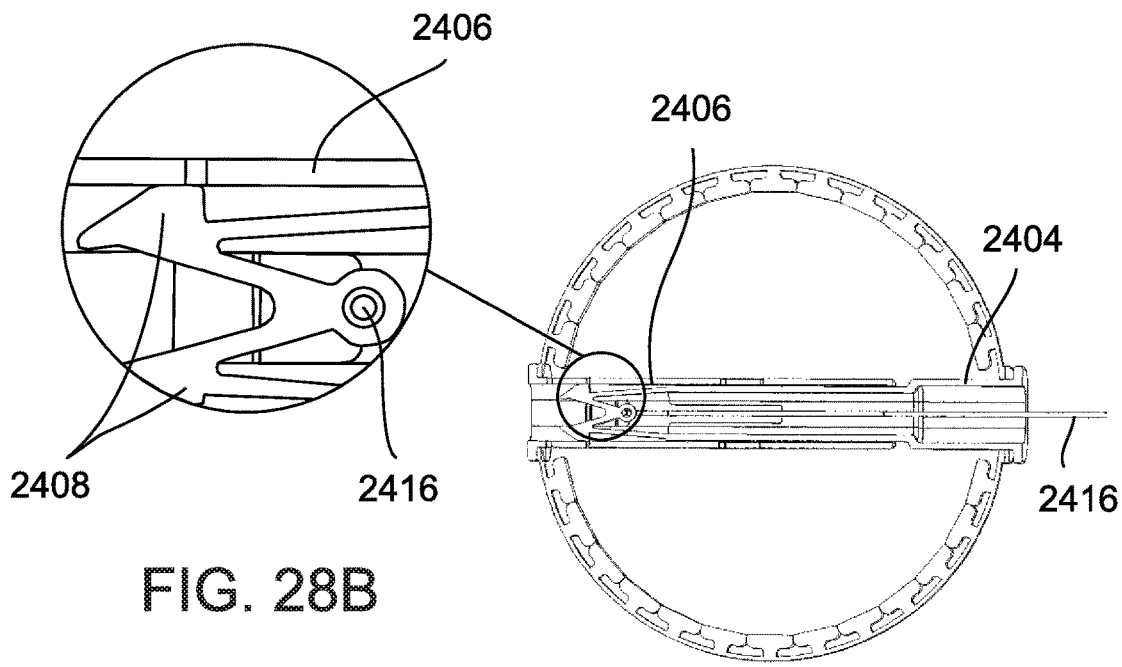
FIG. 28B
FIG. 28A

THREE DIMENSIONAL DEVICES AND METHODS FOR PROLAPSE ALLEVIATION

RELATED APPLICATIONS

This application is a National Phase of PCT Patent Application No. PCT/IL2016/051113 having International filing date of Oct. 13, 2016, which claims the benefit of priority under 35 USC § 119(e) of U.S. Provisional Patent Application No. 62/240,572 filed on Oct. 13, 2015. The contents of the above applications are all incorporated by reference as if fully set forth herein in their entirety.

FIELD AND BACKGROUND OF THE INVENTION

The present invention, in some embodiments thereof, relates to the health care industry and, more particularly, but not exclusively, to devices and methods for treating feminine pelvic organ prolapse.

Pelvic organ prolapse occurs when the network of muscles, ligaments, and tissues that hold the pelvic organs in place is weakened and one or more pelvic organs descend into the vaginal cavity. Pelvic organ prolapse occurs as a result of normal aging, childbirth, pelvic surgery or trauma, and may include one or more of the following conditions:

i) Cystocele, the leading form of pelvic organ prolapse, wherein the bladder drops into the vagina and may be associated with urination problems;

ii) Rectocele, wherein the rectum herniates into the vagina and may result in difficulty and/or pain with defecation;

iii) Enterocele, wherein the small intestine prolapses into the vagina;

iv) Uterine prolapse wherein the uterus drops downward into the vagina and is often associated with other organ prolapse; and v) Vaginal vault prolapse, wherein the top portion of the vagina, the apex, loses its natural shape and drops down into the lower vaginal canal, and may occur in women who had a hysterectomy.

To avoid surgical procedures to treat pelvic organ prolapse, a number of non-surgical vaginal devices, pessaries, have been designed to be inserted into the vagina by a surgeon, medical assistant or user.

Background art includes the following patents, the contents of all of which are incorporated by reference as if fully set forth herein:

WO 2009/130702: Pessaries for Prolapse Alleviation;
U.S. Pat. No. 8,651,109: Pessaries for Prolapse Alleviation;
WO 9601084: Inflatable Vaginal Pessary;
GB 235218: Inflatable Pessary;
FR 2843700: Rehabilitation Device for Urinary and Faecal Continence;
WO 03047476: Vaginal Pessary;
GB 1115727: Apparatus Controlling Incontinence in the Female;
U.S. Pat. No. 5,224,494: Vaginal Pessary;
U.S. Pat. No. 6,158,435: Pessary;
US 2003149334: Vaginal Pessary;
JP 6133996: Pessary for Treating Prolapse of Uterus;
U.S. Pat. No. 4,823,814: Pessary;
U.S. Pat. No. 5,771,899: Pessary;
U.S. Pat. No. 5,894,842: Pessary for Treating Vaginal Prolapse;
U.S. Pat. No. 6,158,435: Pessary;
U.S. Pat. No. 6,216,698: Flexible Pessary;
U.S. Pat. No. 6,503,190: Vaginal Pessary;
U.S. Pat. No. 6,808,485: Compressible Resilient Vaginal Incontinence Insert; and
U.S. Pat. No. 7,036,511: Vaginal Pessary.

SUMMARY OF THE INVENTION

There is provided, in an accordance with an exemplary embodiment of the invention, a device sized and shaped for alleviating pelvic organ prolapse when inserted into a vagina, comprising: a treatment rendering portion configured to be adjustable between a first, collapsed state and a second, expanded state, where the second expanded state extends substantially in three dimensions.

In an embodiment of the invention, the treatment rendering portion comprises a plurality of bendable arcs.

In an embodiment of the invention, the device further comprises an external tube and an internal tube coaxial with and slidable within the external tube.

In an embodiment of the invention, distal ends of the bendable arcs are connected to the external tube and proximal ends of the bendable arcs are connected to the internal tube.

In an embodiment of the invention, proximal ends of the bendable arcs are integral with the internal tube and distal ends of the bendable arcs are connected to the external tube.

In an embodiment of the invention, the internal tube and the external tube releasably interlock to prevent sliding when in the expanded state.

In an embodiment of the invention, the external tube is configured with a slot within which at least one locking pin of the internal tube is received to interlock the external and internal tubes.

In an embodiment of the invention, the treatment rendering portion is an outer bar tube with a distal end connected to an upper tube and with a proximal end connected to a lower tube, where the lower tube is coaxial and slidable within the upper tube and where the upper and lower tubes are coaxial and internal to the outer bar tube.

In an embodiment of the invention, the upper tube and the lower tube releasably interlock to prevent sliding when in the expanded state.

In an embodiment of the invention, the upper tube is configured with a slot within which at least one locking pin of the lower tube is received to interlock the upper and lower tubes.

In an embodiment of the invention, the treatment rendering portion comprises a spiral cut tube, with a distal end connected to an upper tube and with a proximal end connected to a lower tube, where the lower tube is coaxial and slidable within the upper tube and where the upper and lower tubes are coaxial and internal to the outer bar tube.

In an embodiment of the invention, the upper tube and the lower tube releasably interlock to prevent sliding when in the expanded state.

In an embodiment of the invention, the upper tube is configured with a slot within which at least one locking pin of the lower tube is received to interlock the upper and lower tubes.

In an embodiment of the invention, the treatment rendering portion comprises at least two component elements, an upper element and a lower element, where the elements are positioned concentrically opposing and orthogonal to each other.

In an embodiment of the invention, the upper element is provided with an outer telescoping tube and the lower element is provided with a toothed, sliding post, where the sliding post slides coaxially within the telescoping tube during device expansion into the expanded state.

In an embodiment of the invention, at least one tooth is provided to a distal end of the sliding post and where the tooth is configured to reversibly lock the device into the expanded state when the at least one tooth moves past a block provided in a slot in the outer telescoping tube.

In an embodiment of the invention, the treatment rendering portion is shaped like a sphere.

In an embodiment of the invention, the treatment rendering portion is shaped like a pear.

In an embodiment of the invention, the treatment rendering portion is shaped like an ovoid.

In an embodiment of the invention, the treatment rendering portion is shaped like a cuboid.

In an embodiment of the invention, the treatment rendering portion is rotationally symmetric.

In an embodiment of the invention, the treatment rendering portion does not exhibit uniform flexibility around its circumference in the expanded state.

In an embodiment of the invention, the treatment rendering portion exhibits a plurality of planes of flexibility.

In an embodiment of the invention, the device is configured to be permeable to vaginal secretions.

In an embodiment of the invention, at least a portion of the treatment rendering portion is provided with a covering.

In an embodiment of the invention, the device further comprises a locking mechanism.

In an embodiment of the invention, the locking mechanism comprises at least one tooth configured to move in a slot, wherein when the slot is provided with a block at least one locking pin is in the window the device is reversibly locked.

In an embodiment of the invention, the locking mechanism comprises at least one locking pin configured as a counterpart to a window or slot, wherein when the at least one locking pin is in the window the device is reversibly locked.

In an embodiment of the invention, the device further comprises a removal device for converting the device from the second, expanded state to the first, collapsed state.

In an embodiment of the invention, the removal device comprises a string.

In an embodiment of the invention, the removal device further comprises a removal disk attached to the string.

In an embodiment of the invention, the removal device further comprises a holding bar attached to the string.

In an embodiment of the invention, the treatment rendering portion comprises three or more plastic arcs connected to two concentric telescopic elements.

In an embodiment of the invention, the treatment rendering portion comprises coaxial telescopic elements and a plurality of block elements.

In an embodiment of the invention, the treatment rendering portion comprises at least two orthogonal ring elements, forming arcs, with a plurality of blocks connected to an internal side of the arcs.

There is further provided in accordance with an exemplary embodiment of the invention, a system for alleviating pelvic organ prolapse when inserted into a vagina, comprising: (a) a device according to claim 1; and, (b) an applicator.

In an embodiment of the invention, the applicator comprises a holder and a puller.

In an embodiment of the invention, a distal end of the puller is configured with a prong for releasably holding the device to the applicator.

In an embodiment of the invention, the puller is configured with snapping teeth for releasably holding the device to the applicator.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and not necessarily to scale, and are for purposes of illustrative discussion of embodiments of the invention. In this regard, the description taken with the drawings makes apparent to those skilled in the art how embodiments of the invention may be practiced.

In the drawings:

FIG. 19A is a cross-sectional view of the device of FIG. 16A, in accordance with an exemplary embodiment of the invention;

FIG. 19B is a close-up, cross-sectional view of a locking mechanism of the device of FIG. 16A, in accordance with an exemplary embodiment of the invention;

FIG. 22 is a front view of a chain made of a plurality of block elements, in accordance with an exemplary embodiment of the invention;

FIG. 23A is a cross-sectional view of the device of FIG. 20A, in accordance with an exemplary embodiment of the invention;

FIG. 23B is a close-up, cross-sectional view of a locking mechanism of the device of FIG. 20A, in accordance with an exemplary embodiment of the invention;

FIG. 27A is a cross-sectional view of the device of FIG. 24A, in accordance with an exemplary embodiment of the invention;

FIG. 27B is a close-up, cross-sectional view of a locking mechanism of the device of FIG. 24A, in accordance with an exemplary embodiment of the invention;

FIG. 28A is a cross-sectional view of the device of FIG. 24A, in pulled removal string state, in accordance with an exemplary embodiment of the invention;

FIG. 28B is a close-up, cross-sectional view of a locking mechanism of the device of FIG. 24A, in pulled removal string state, in accordance with an exemplary embodiment of the invention;

DESCRIPTION OF SPECIFIC EMBODIMENTS OF THE INVENTION

Figures 1A, 1B:
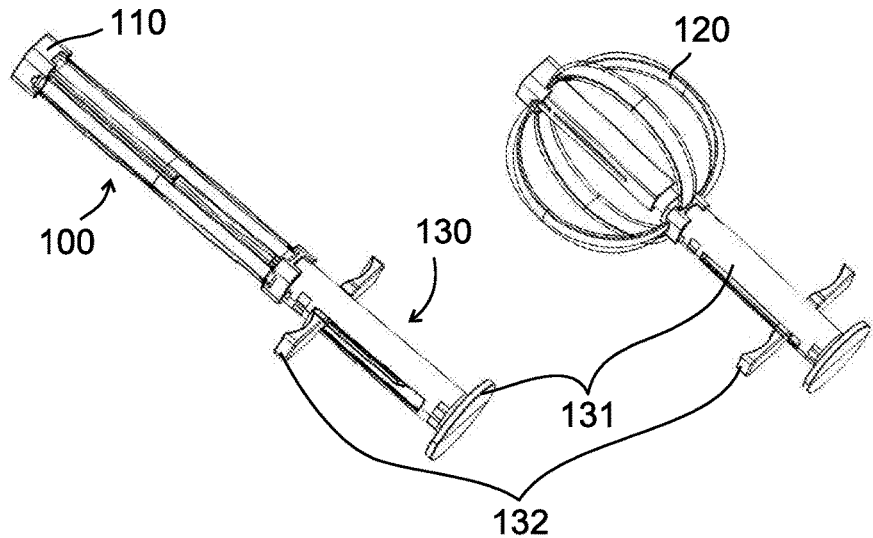
FIGS. 1A-1B are perspective views of a collapsed and open, respectively, ball-type prolapse treating device with individual arcs connected to two tubes and attached to an applicator, in accordance with an exemplary embodiment of the invention.

The present invention, in some embodiments thereof, relates to the health care industry and, more particularly, but not exclusively, to devices and methods for treating feminine pelvic organ prolapse.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways. It should also be understood that in this specification, "distal" or "distally" means in the direction of or on the side of the cervix and "proximal" or "proximally" means in the direction of or on the side of the vaginal introitus.

The Devices Generally

In general, devices and methods are described for the treatment of feminine pelvic organ prolapse. It should be understood that features, forms and/or functions overlap among some or many of the embodiments that will be described herein and that description in relation to one embodiment may also apply to others. For brevity and efficiency, many of these common features and/or forms and/or functions are described only in this "Generally" section but apply to one, some or all embodiments. Specific distinctions between embodiments in features, form and/or function are described in additional sections below.

In some embodiments of the invention, the devices described herein are generally three dimensional (extend substantially in 3 dimensions) and/or are rotationally symmetric and/or are not rotation sensitive in order to render treatment. In some embodiments of the invention, the device is ball/spherical, pear, box/cube/cuboid, ovoid shaped or the like. Throughout the specification, where "ball" is used, it could mean any conceivable three dimensional shape appropriate for rendering prolapse treatment, for example any of those described above. Different exemplary device embodiments are described in detail below.

The device, or at least the ball portion of the device, is constructed of a plurality of arc sections, optionally 3 or more, where in the case of 3 arcs, each arc defining a dimension of the device, in an embodiment of the invention. In some embodiments of the invention, at least the arcs of the device are constructed of a bio-compatible material or materials and, optionally, of a material or materials which do not facilitate vaginal flora changes. Exemplary materials include high density polyurethane (for the plastic/skeletal part) and thermoplastic elastomers or silicone for the covering. In some embodiments of the invention, the device is configured to be permeable or to allow vaginal secretions to exit the vagina.

In some embodiments of the invention, the external surface of the device is smooth, for example to increase comfort to the user, reduced accumulated discharge and/or reduce the production of biofilms.

In an embodiment of the invention, at least one arc of the ball portion is at least partially covered by a padding or exterior layer (which would then be the external surface of the device, taking the place of the at least one arc itself as the external surface). Optionally, the layer is configured to at least enhance user comfort and/or to reduce or prevent tissue necrosis. Optionally, the layer is configured to permit vaginal secretions to exit the vagina. Optionally, the layer is rigid.

In some embodiments of the invention, a removal string is operatively connected to the device to enable a user to displace the device from the vagina and remove it from her body.

In an embodiment of the invention, a locking mechanism is provided to the device, for example to enable the device to lock into an expanded and/or closed state. Different exemplary locking mechanism embodiments are described below, for example including snapping elements and/or pins and/or teeth and/or slots and/or windows. In some embodiments of the invention, the device is bi-stable. Optionally the bi-stable feature is facilitated by the locking mechanism. In some embodiments of the invention, the locking mechanism is activated by an applicator used for inserting the device. In some embodiments of the invention, the locking mechanism is deactivated by the removal string. In some embodiments of the invention, the locking mechanism is activated and/or deactivated by something other than mechanical forces, for example using magnetic, electric, pneumatic, and/or hydraulic force.

The devices described herein are configured to accommodate a plurality of vaginal sizes and/or shapes, in some embodiments of the invention. For example, the devices optionally are provided in a variety of sizes and/or shapes and/or flexibilities.

In some embodiments of the invention, device shape is predefined but not permanent, that is, once deployed inside the patient the flexibility of the device allows some shape matching to the user's individual anatomical features. In some embodiments of the invention, a range of devices will exhibit in the expanded state diameters of 40-75 mm (the diameter pertains to the maximal distance between two opposite elements of the device in contact with the vagina). In some embodiments of the invention, devices exhibit a collapsed diameter of 35 mm or less.

In some embodiments of the invention, the device does not exhibit a uniform flexibility around the circumference of the device. For example, the device is rigid in two dimensions (in a plane) at 0° and 180° (going around arcs or arms of the device) but is flexible at all other points. As another example, the device is rigid in two dimensions (defining a plane of flexibility) at 0° and 180°, is less rigid at 90° and 270° and is flexible elsewhere. In some embodiments of the invention, the arcs or arms of the device increase in rigidity towards 0° and 180° and increase in flexibility towards 90° and 270°. In some embodiments of the invention, the device is configured such that mirror image portions of arcs or arms of the device (any subsection up to and between 180°) flex towards each other. It should be understood that flexibility can be demonstrated selectively anywhere around the circumference of the arms or arcs, for example at 45° and/or 135° additionally and/or alternatively to 90° and 270°. In some embodiments of the invention, the device exhibits alternating and/or regular rigidity and flexibility around the circumference of the device. In some embodiments of the invention, flexibility of the device corresponds to planes of flexibility, for example in a three dimensional device there could be three major planes of flexibility. Optionally, the flexibility around the circumference of the device is configured so that the device will exhibit a particular desired shape, for example arcs that are more flexible at the distal end than at the proximal end might imbue a pear shape to the device when expanded.

It should be understood that these are examples only, and that any combination of rigidity and flexibility, including no rigidity or no flexibility are permitted, depending on the intended use and/or needs of the user.

In some embodiments of the invention, sizes and/or shapes and/or flexibilities are chosen to reduce pressure on vaginal walls and/or provide better force distribution of the device on vaginal walls and/or to reduce the probability of pressure necrosis, optionally in combination with the padded covering/exterior layer.

In some embodiments of the invention, the device and the applicator, together, comprise a system for inserting and deploying the prolapse alleviating device.

In some embodiments of the invention, the device is offered in a plurality of sizes and/or determination of which specific device is most appropriate for a certain user is performed by a sizing device configured for indicating a device size to the user or to an attending medical professional. In some embodiments of the invention, the sizing device changes diameter and/or state to known device sizes and/or states in order to determine the proper device that should be used by the user. In some embodiments of the invention, a "fit-kit", comprised of a plurality of different sized devices (or dummies representing different device sizes), is used by the patient to self-diagnose the proper size by trying out the different sizes until the most appropriate one is found. In some embodiments of the invention, an attending medical professional uses the fit-kit.

In some embodiments of the invention, the device is disposed of after use. In some embodiments of the invention, the device is reusable and/or configured to be reused (for example, is washable/sterilizable).

Function and Modes of Operation

In some embodiments of the invention, operation of the devices described herein can be divided into three general phases: i.) insertion/deployment, ii.) use (i.e. wearing the device), and iii.) removal.

With respect to insertion, devices are inserted with a particular predetermined orientation (or with orientation assistance) or are not sensitive to insertion orientation (e.g. are rotationally symmetrical), depending on the particular embodiment. In some embodiments of the invention, devices described herein are inserted in a closed, compacted and/or collapsed state for ease of storage and/or insertion.

In some embodiments of the invention, devices are inserted manually, without an applicator. Optionally, the user or a caregiver inserts the device manually. In some embodiments of the invention, devices are inserted with an applicator, which optionally also assists with orientation and/or deployment/expansion of the device. In some embodiments of the invention, depth of insertion is a factor to be considered.

Optionally, an applicator used for inserting a device is configured, for example the grip of the applicator is located such that proper insertion depth is established when the patient inserts the device until the fingers holding the applicator touch the labia. In some embodiments of the invention, the applicator is disposed of after device insertion and/or deployment.

In some embodiments of the invention, at least one of the devices (optionally including an applicator) described herein is configured to be inserted and/or deployed with only one hand. In other cases the applicator may be held with two hands (fingers 1+3 of both hands, and the plunger pushed forward with the 2 index fingers, or held with two hands and plunger pushed with one index finger. In some embodiments of the invention, at least one device (optionally including an applicator) is configured to be insertable and/or deployable regardless of the user's position, for example while the user is in a supine, standing or sitting position. In some embodiments of the invention, at least one device (optionally including an applicator) is configured to be insertable and/or deployable minimizing user self-touching. For example, the user does not have to separate the labia in order to insert the device and/or does not need to insert fingers into the vagina in order to position the device.

With respect to usage of the devices described herein, in some embodiments of the invention they are inserted into the user in order to treat pelvic organ prolapse and/or to support the vaginal walls, that is, to provide support from the vagina against organs sagging down into the vaginal canal. In some embodiments of the invention, devices described herein are expanded and/or change state for use. In some embodiments of the invention, the devices described herein treat pelvic organ prolapse by stretching vaginal walls, optionally laterally, flattening the anterior and posterior vaginal walls and thereby reducing anterior and posterior prolapse. In some embodiments of the invention, a space occupying characteristic of the devices described herein treat apical prolapse, whereby the vaginal apex (uterine/vault) is not allowed to descend. The devices described herein are removed after insertion periodically. Optionally, the devices herein are reusable. In some embodiments of the invention, the devices described herein are configured to elute pharmaceutical substances into the user.

With respect to removal of the devices described herein, the devices change from an expanded and/or deployed state into a closed, compacted and/or collapsed state for ease of removal. Optionally the removal state/configuration is the same as the storage/insertion state/configuration. In some embodiments of the invention, removal is effectuated by pulling on a removal string which is operatively connected to the device. Optionally, forces applied to the removal string are configured to also cause state/configuration change of the device from an expanded state to a collapsed state.

Optionally, in cases where vaginal walls are lax, a pull of the string will cause extraction of the device still in its deployed state, somewhat deformed due to its flexibility, before the pulling force on the locking mechanism comes into action. This depends on the resistance of the vaginal introitus, and when absent—the device may be removed painlessly and/or even without collapse.

Exemplary Device Embodiments

FIGS. 1A-1B are perspective views of a collapsed and open, respectively, ball-type prolapse treating device 100 with individual arcs 102 connected to two tubes 104 (shown and described in more detail with respect to FIG. 2), 108 and attached to an applicator 130, in accordance with an exemplary embodiment of the invention. As shown in FIG. 1A and FIG. 1B, the device 100 is configured to transform from a collapsed state 110 to an expanded state 120. In some embodiments of the invention, the device 100 assumes the collapsed state 110 during storage, insertion and/or removal. In some embodiments of the invention, the device 100 assumes the expanded state 120 after insertion and/or during use to support at least one prolapsed organ from within the vagina.

Figure 2:
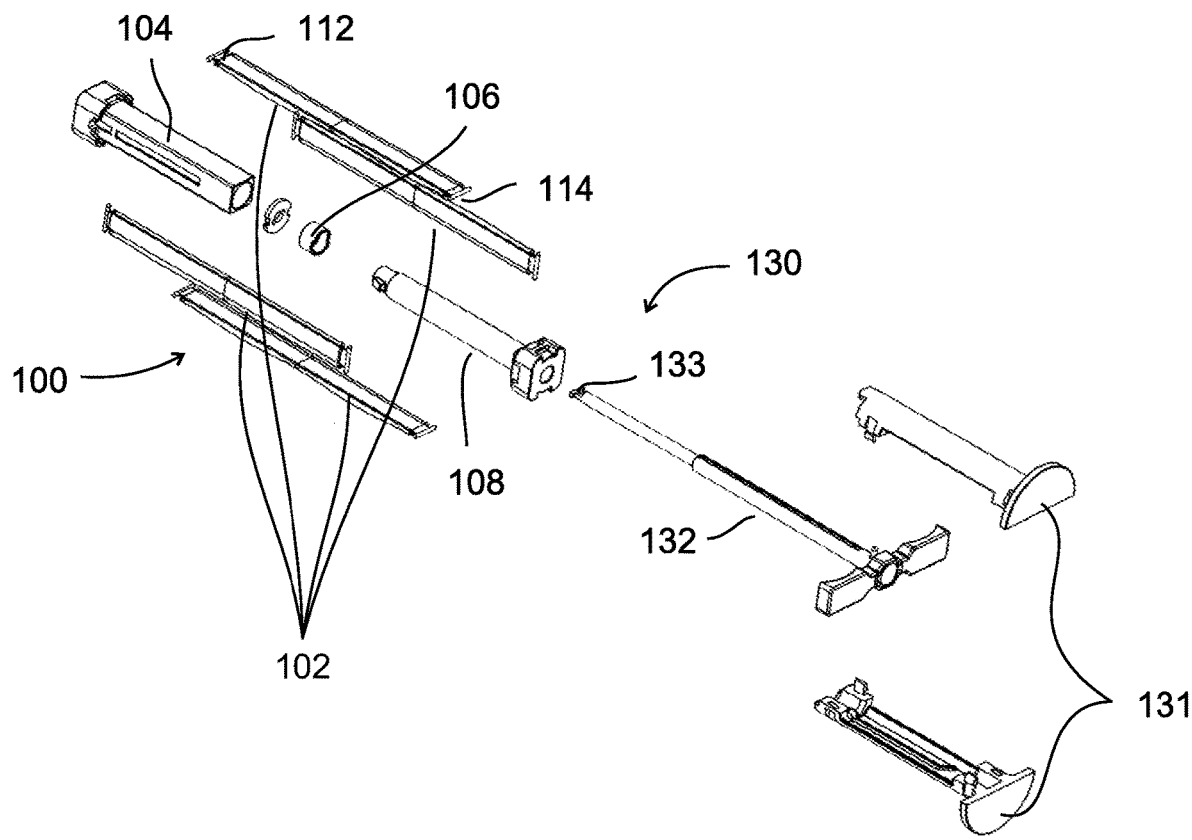
FIG. 2 is an exploded view of the collapsed ball-type prolapse treating device with individual arcs between two tubes and the applicator of FIG. 1A, in accordance with an exemplary embodiment of the invention.

FIG. 2 is an exploded view of the collapsed ball-type prolapse treating device 100 and the applicator 130 of FIG. 1A, in accordance with an exemplary embodiment of the invention. As shown in the exploded view, the device comprises 3 or more (in this embodiment, 4) bendable arcs 102 whose ends are secured by two telescoping tubes 104, 108, where the top end (distal end) 112 of the arcs 102 attach to an outer tube 104 and the bottom end (proximal end) 114 of the arcs 102 attach to an inner tube 108. In an embodiment of the invention, telescoping means the inner tube 108 slides within the outer tube 104 to adjust the overall length of the device 100 and/or the flex or degree of bending of the arcs 102. It should be understood that while the tubes 104, 108 are called "tubes" which would imply a cylindrical shape, they are not necessarily cylindrical. For example, outer tube 104 has a square shaped cross-sectional profile in FIG. 2. In an embodiment of the invention, the outer tube 104 has slots leading snapping pins on the inner tube 108. The snapping pins 109, shown in FIGS. 3B-3C, serve as a locking mechanism by contracting inwards at the end of the slots and moving back to their original position in locking slots in-line with the leading slots.

In an embodiment of the invention, the arcs 102 are covered by an elastic material layer 116 that serves as padding to reduce pressure on the vaginal tissue.

In an embodiment of the invention, the applicator 130 is attached to the device 100 and used for insertion the device 100 into a vagina and/or for transforming the device 100 from the collapsed state 110 into the expanded, ball-like state 120. In an embodiment of the invention, the applicator 130 includes at least two main components, a pessary holder 131 and a puller 132. The holder 131 and puller 132 are configured to allow axial movement of the puller 132 relative to the holder 131, where the puller 132 moves axially within the holder 131. Pulling the puller 132 in a proximal direction causes the distal end of the device 100 to move towards the proximal side of the device 100, thereby shortening its overall length and causing an outward bowing or expansion of the arcs 102.

The puller 132 is removably attached to the outer tube 104 such that the puller 132 can be selectively released from the outer tube 104 (for example, after the device 100 has been deployed and the applicator 130 is being removed from the vagina, leaving the device in situ). Optionally, the puller 132 and the outer tube 104 are configured as counterparts with a screwing action that can be detached by rotation, for example where a prong 133 on the distal end of the puller 132 rotates within a threaded groove in the outer tube 104 to achieve this effect. In some embodiments of the invention, the holder 131 has an internal rail which leads the prong 133 to the threading only after the puller 132 has slid within the holder 131 sufficiently to expand the device 100 into its expanded state 120. In some embodiments of the invention, the device is reversibly locked in its ball state (described in more detail below with respect to FIGS. 3A-3C). In an embodiment of the invention, when the applicator 130 is removed a removal string's 120 free (proximal) end extends outside the vagina (similar to a conventional menstrual tampon).

Figure 3A:
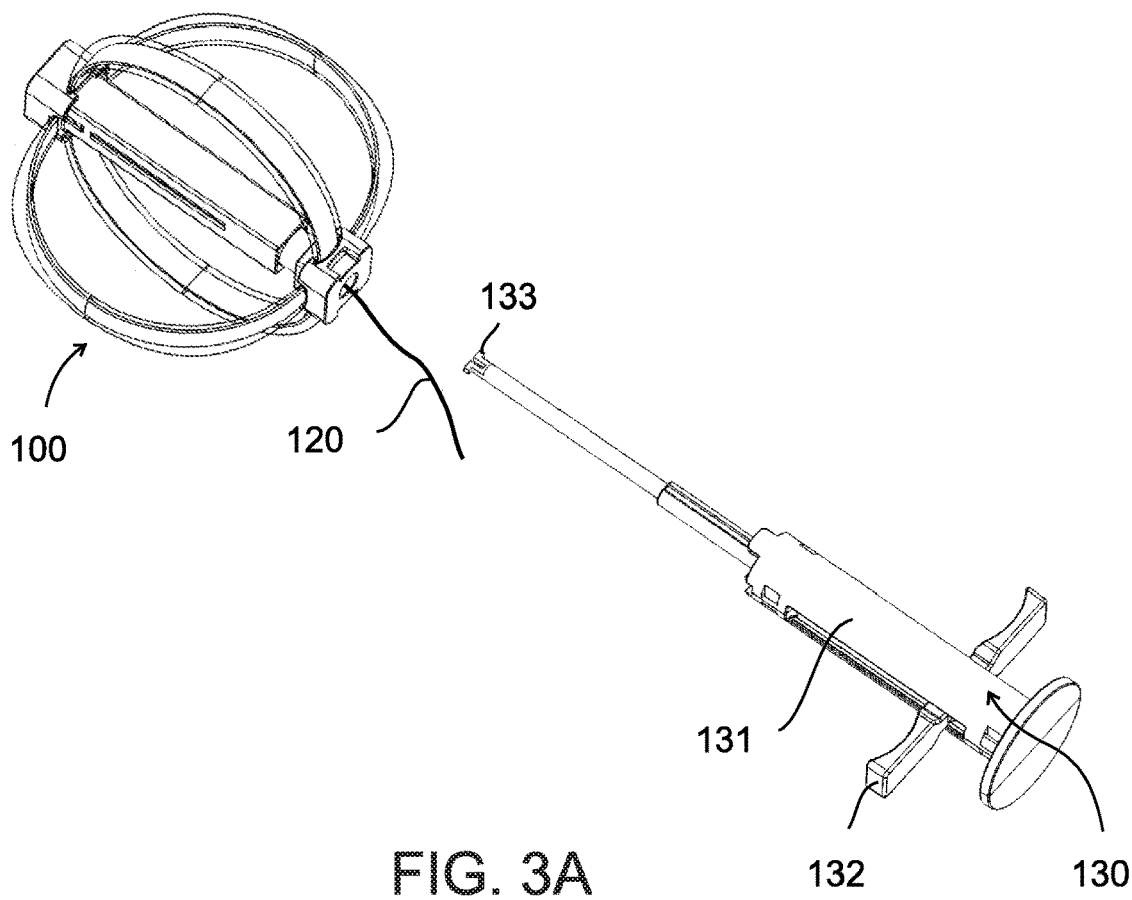
FIG. 3A is a perspective view of the prolapse treating device of FIG. 1B separated/deployed from the applicator, in accordance with an exemplary embodiment of the invention.
Figure 3B:
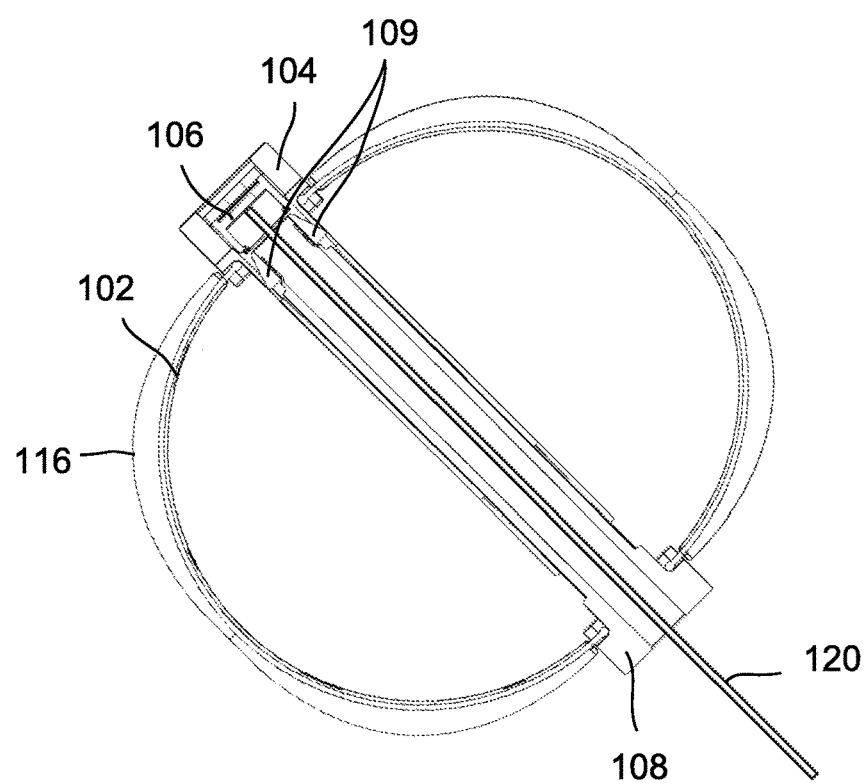
FIGS. 3B-3C are cross-sectional views of the device of FIG. 1B separated/deployed from the applicator, in accordance with an exemplary embodiment of the invention.
Figure 3C:
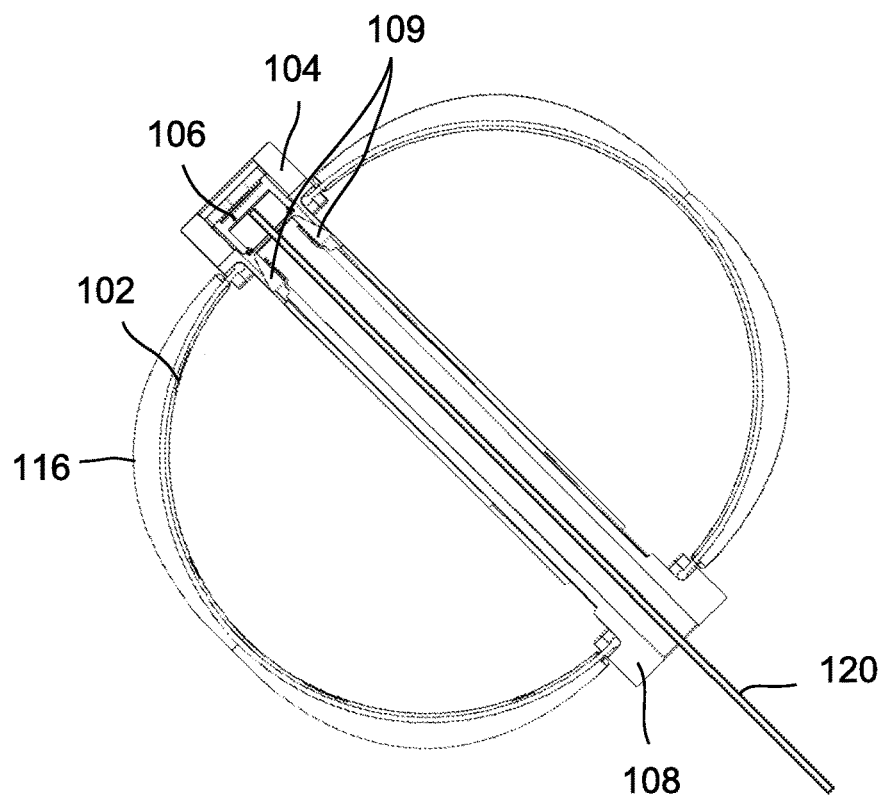

FIG. 3A is a perspective view of the prolapse treating device 100 of FIG. 1B separated/deployed from the applicator 130, in accordance with an exemplary embodiment of the invention. To remove the pessary from the vagina, in an embodiment of the invention, the removal string 120 connected to a removal disk 106 is pulled. The removal disk 106 is configured to collapse on locking pins 109, pressing the locking pins towards a central axis of the device 100 and thus releasing the locking mechanism. Unlocking the locking mechanism allows the device 100 to transform from the ball state 120 back to the collapsed state 110 for easier removal which is achieved by a sustained proximal on the removal string 120.

Figures 4A, 4B:
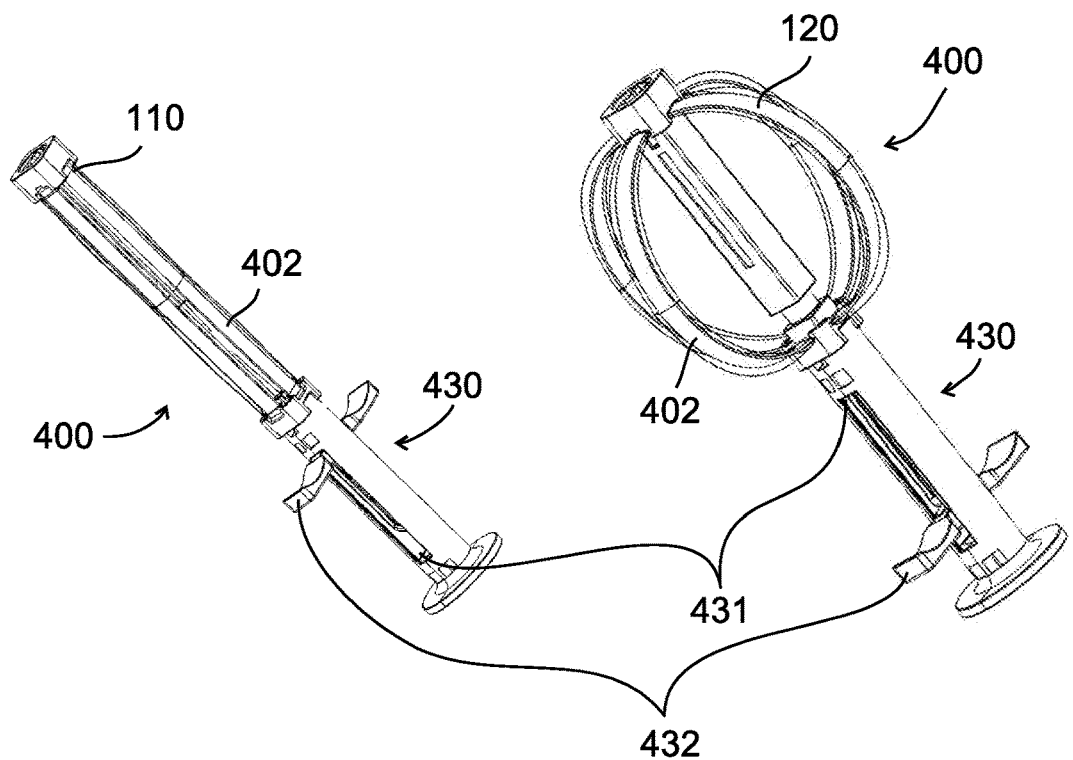
FIGS. 4A-4B are perspective views of a collapsed and open, respectively, ball-type prolapse treating device with individual arcs integrated with one of two tubes and attached to an applicator, in accordance with an exemplary embodiment of the invention.
Figure 5:
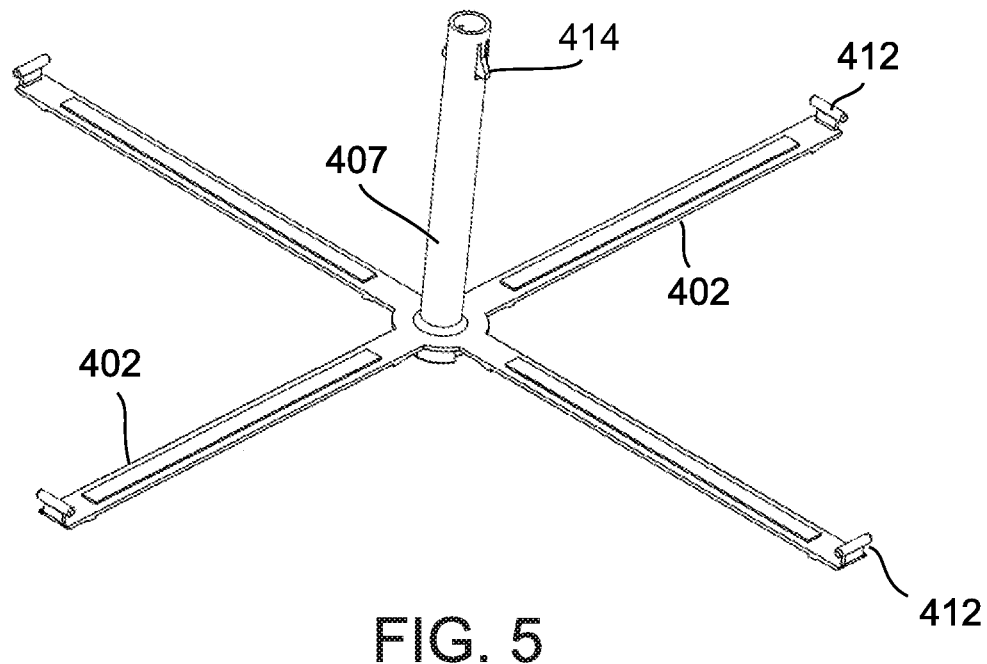
FIG. 5 is a perspective view of the lower tube with integrated arcs of FIGS. 4A-4B, in accordance with an exemplary embodiment of the invention.

FIGS. 4A-4B are perspective views of a collapsed and open, respectively, ball-type prolapse treating device 400 with 3 or more individual arcs 402 integrated with one 407 of two tubes and attached to an applicator 430, in accordance with an exemplary embodiment of the invention. As with other embodiments described herein, the device 400 is configured to assume a plurality of stable states (e.g. compressed and expanded). In an embodiment of the invention, the arcs 402 are an integrated component of an inner tube 407 of the device, shown and described in more detail with respect to FIG. 5, where the proximal ends of the arcs 402 are integrated into the inner tube 407. In some embodiments of the invention, the distal ends 412 of the arcs 402 are configured to connect to an outer tube 409 within which the inner tube 407 is axially located and slidable within, telescopically.

In an embodiment of the invention, an applicator 430 is attached to the device 400 and used for insertion of the device 400 into a vagina and/or for transforming the device from the collapsed state 110 into the expanded, ball like state 420. The applicator 430 is constructed similarly to the applicator 430 of FIG. 1A, including a holder 431 and a puller 432, and functions largely in a similar manner. In an embodiment of the invention, when the applicator 430 is removed a removal string's 410 free (proximal) end extends outside the vagina (similar to a conventional menstrual tampon).

As with other embodiments described herein, by pulling the removal string 410, the removal disk 406 is contracted, bending locking pins 414 (shown in more detail in FIGS. 5 and 6) inwards towards a central axis of the device and out of counterpart slots on the outer tube 409. Bending the locking pins 414 inwards releases the outer tube 409 from the inner tube 407, thus allowing the tubes to slide relative to each other and returning the device 400 to something akin to the collapsed state 110 and facilitating easy removal of the device 400 out of the vagina.

Figure 6:
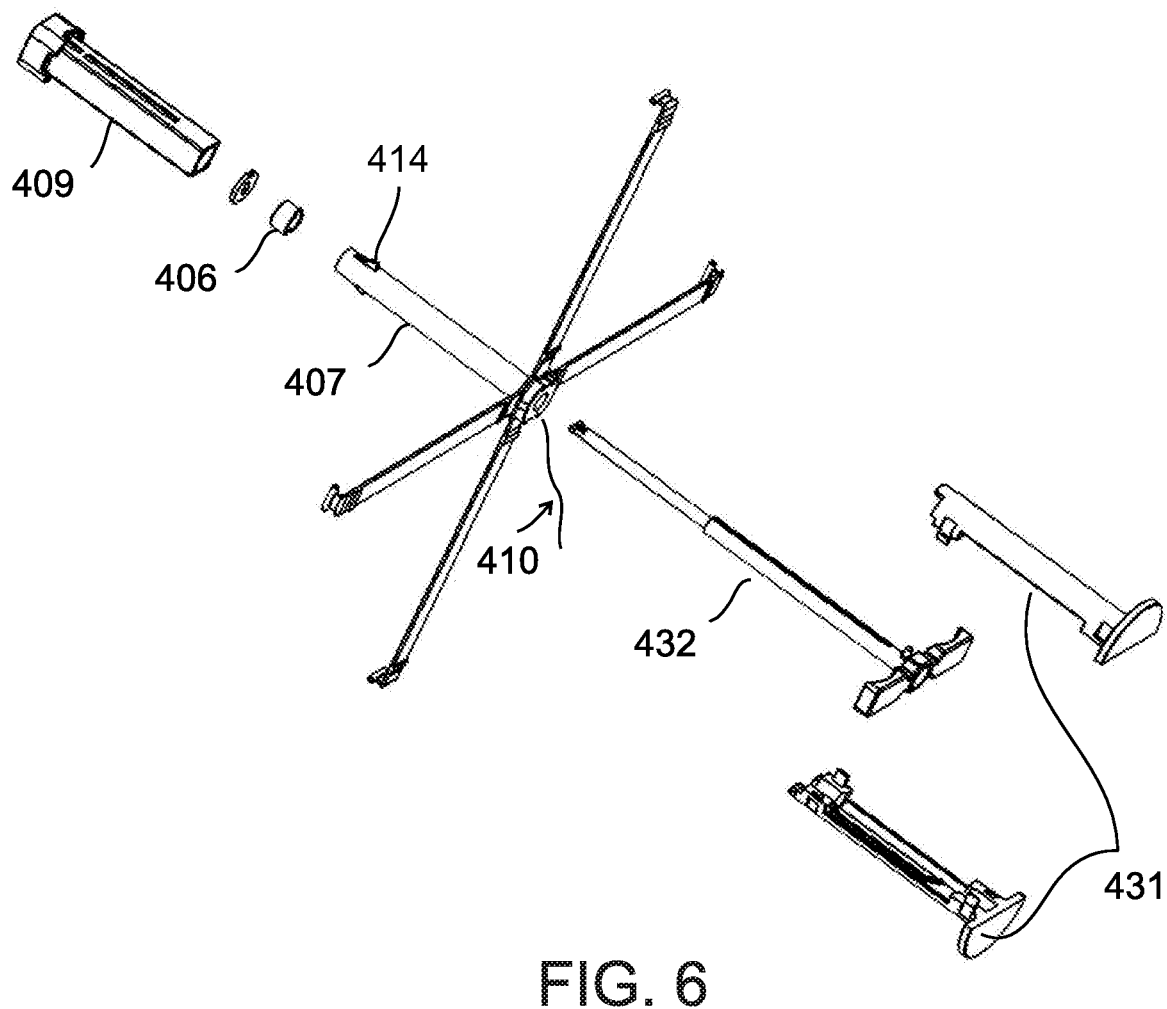
FIG. 6 is an exploded view of the collapsed ball-type prolapse treating device and the applicator of FIG. 4A, in accordance with an exemplary embodiment of the invention.

FIG. 6 is an exploded view of the ball-type prolapse treating device 400 and the applicator 430 of FIG. 4A, in accordance with an exemplary embodiment of the invention.

Figures 7A, 7B:
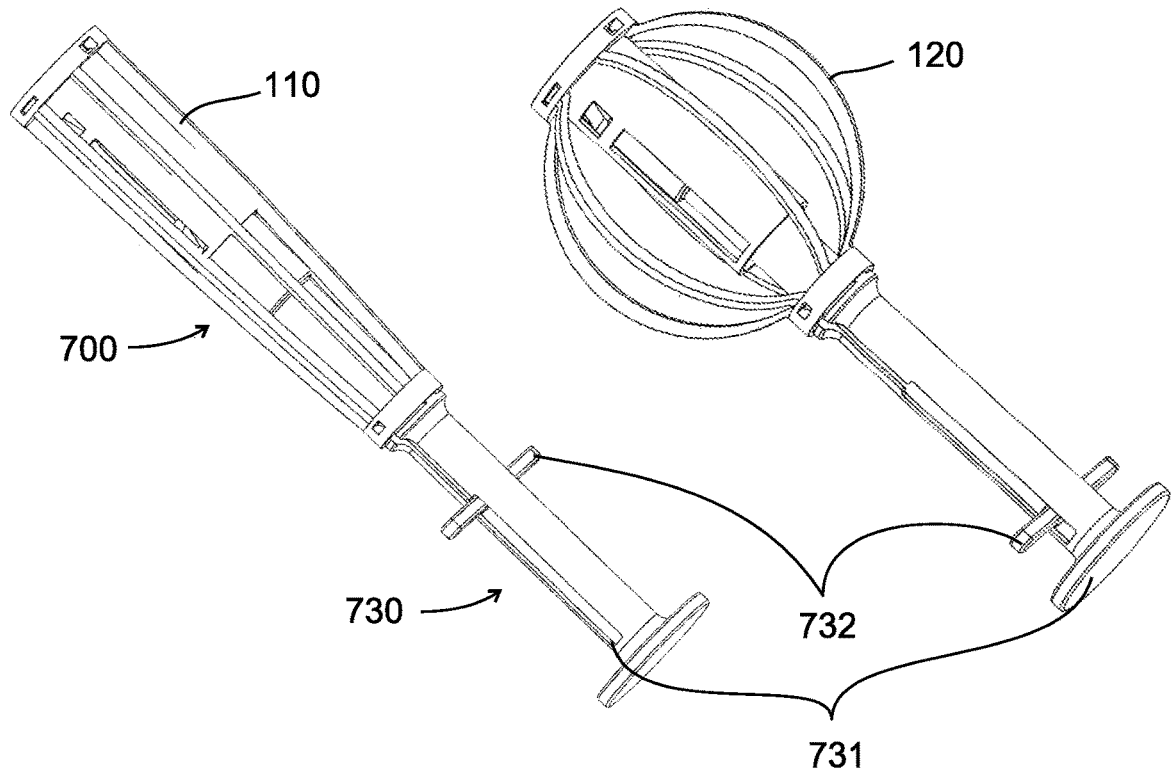
FIGS. 7A-7B are perspective closed and open, respectively, views of a ball-type prolapse treating device with an outer bar tube attached to an applicator, in accordance with an exemplary embodiment of the invention.

FIGS. 7A-7B are perspective closed and open, respectively, views of a ball-type prolapse treating device 700 with an outer bar tube 702 attached to an applicator 730, in accordance with an exemplary embodiment of the invention. In an embodiment of the invention, the device 700 is configured to transition from a first collapsed state 110 to a second, expanded state 120. As with other embodiments described herein, the first state 110 is used during storage, insertion and/or removal of the device 700 and the second state 120 is used after deployment to render treatment to the user. In an embodiment of the invention, both states are stable.

In an embodiment of the invention, the applicator 730 is attached to the device 700 and used for insertion of the device 700 into a vagina and/or for transforming the device from the collapsed state 110 into the expanded, ball like state 120. The applicator 730 includes a holder 731 and a puller 732, shown in more detail in FIG. 8, in an embodiment of the invention. In an embodiment of the invention, the holder 731 and puller 732 are assembled in a way that allows co-axial movement of the puller 732 within and relative to the holder 731. The puller 732 is held within slots 733 of the upper tube 734, in an embodiment of the invention. The puller 732 pulls the upper tube 734 in a proximal direction until the upper tube 734 locks into a lower tube 735, forming the arcs of the outer bar tube 702 into the expanded ball state 120. Upon expansion of the device 700, the arms of the puller 732 come with contact with the lower tube 735 and bend inwards. Thus, the puller 732 is detached from the slots 733 and is removed together with the holder 731, leaving the device inside the user's vagina.

In an embodiment of the invention, when the applicator 730 is removed a removal string's 710 free (proximal) end extends outside the vagina (similar to a conventional menstrual tampon).

Figure 8:
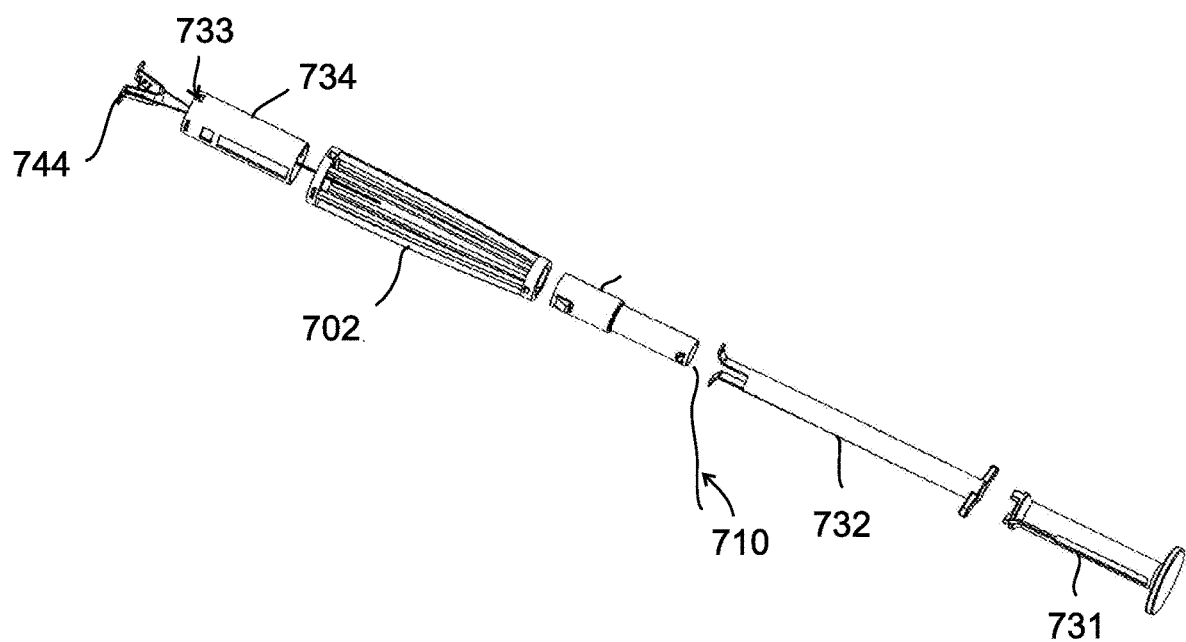
FIG. 8 is an exploded view of the ball-type prolapse treating device and the applicator of FIG. 7A, in accordance with an exemplary embodiment of the invention.

FIG. 8 is an exploded view of the ball-type prolapse treating device 700 and the applicator 730 of FIG. 7A, in accordance with an exemplary embodiment of the invention. In an embodiment of the invention, the outer bar tube 702 is connected on the upper or distal end to the upper tube 734 and the lower or proximal end is connected to the lower tube 735. In some embodiments of the invention, a "V" shaped bar 744 holds the upper telescopic tube 734 together with the outer bar tube 703.

Figures 9A, 9B:
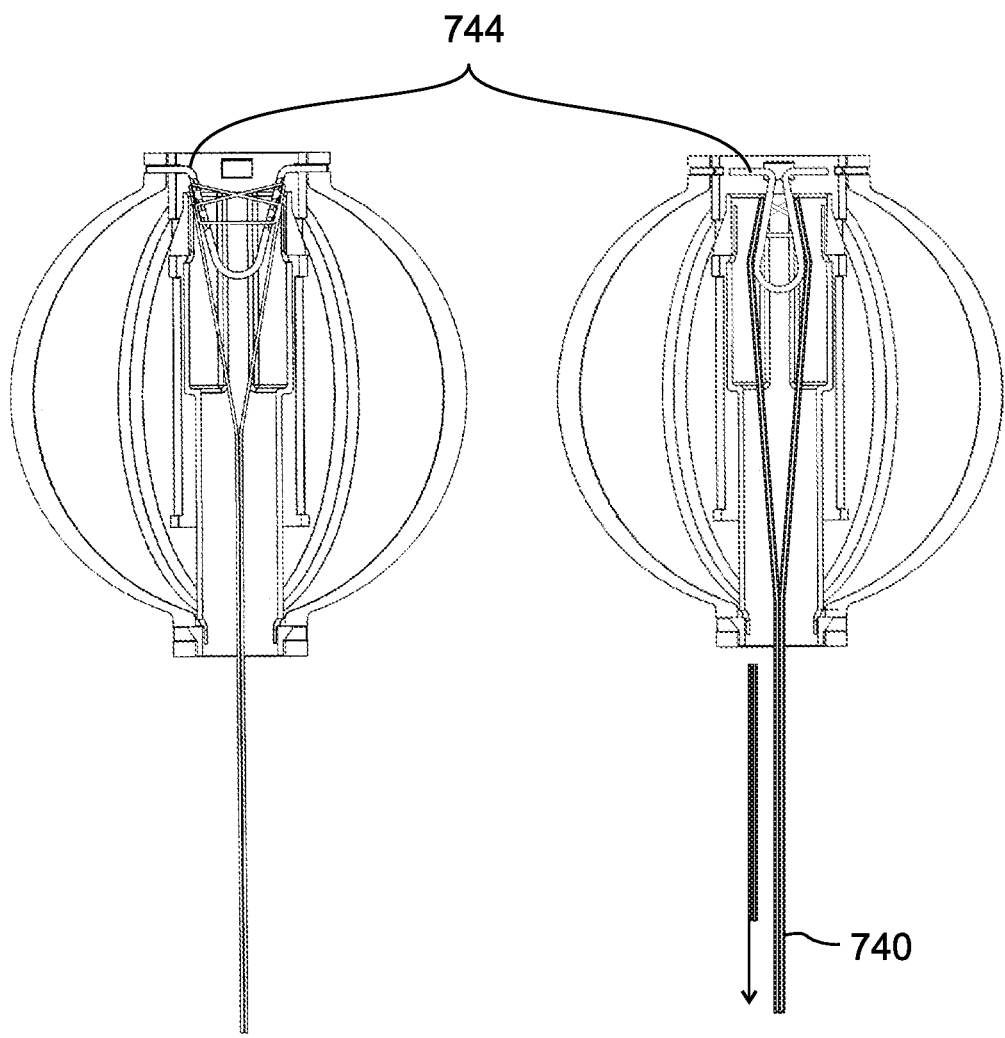
FIGS. 9A-9B are side views of the ball-type device of FIG. 7B showing a holding bar extended and retracted, respectively, in accordance with an exemplary embodiment of the invention.

FIGS. 9A-9B are side views of the ball-type device of FIG. 7B showing a holding bar extended and retracted, respectively, in accordance with an exemplary embodiment of the invention. To remove the device 700 from the user's vagina, a removal string 740 connected to the bar 744 is pulled in a proximal direction, causing a deflection of the bar 744, releasing the now-connected telescopic tubes 734, 735 from the outer tube 702 and converting the device 700 from the expanded, ball state 120 to the collapsed state 110.

Figures 10A, 10B:
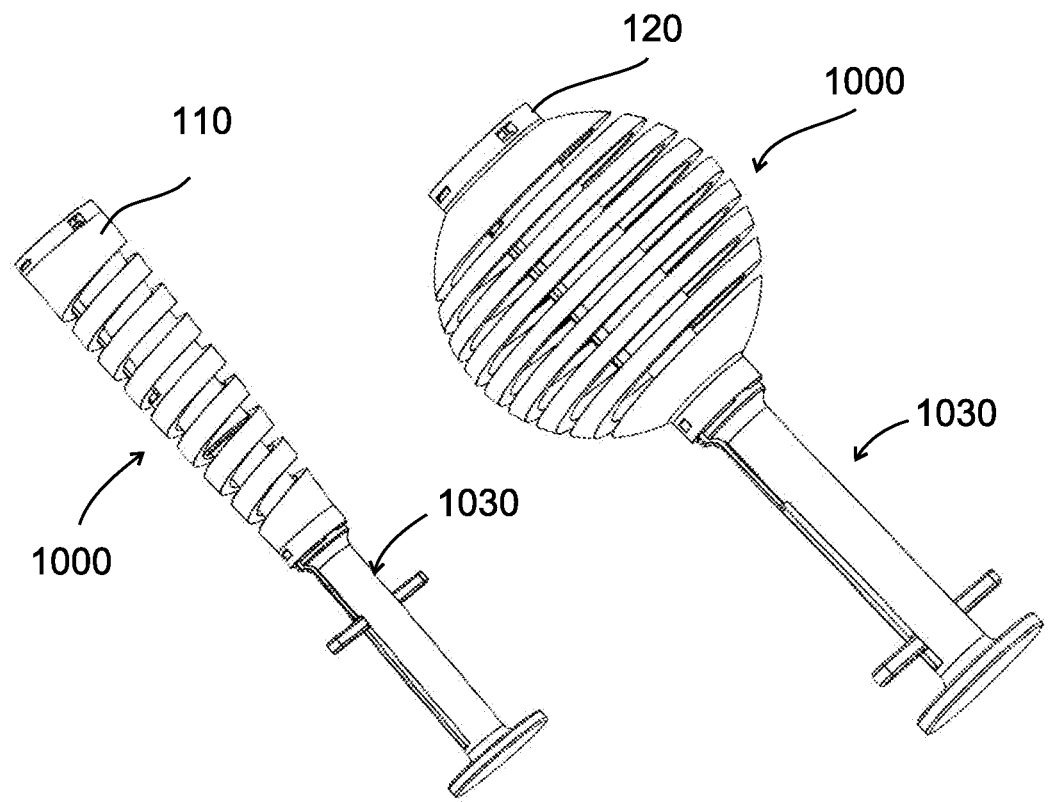
FIGS. 10A-10B are perspective closed and open, respectively, views of a ball-type prolapse treating device with an outer spiral tube attached to an applicator, in accordance with an exemplary embodiment of the invention.

FIGS. 10A-10B are perspective closed 110 and open 120, respectively, views of a ball-type prolapse treating device 1000 with an outer spiral tube 1046 attached to an applicator 1030, in accordance with an exemplary embodiment of the invention.

Figure 11:
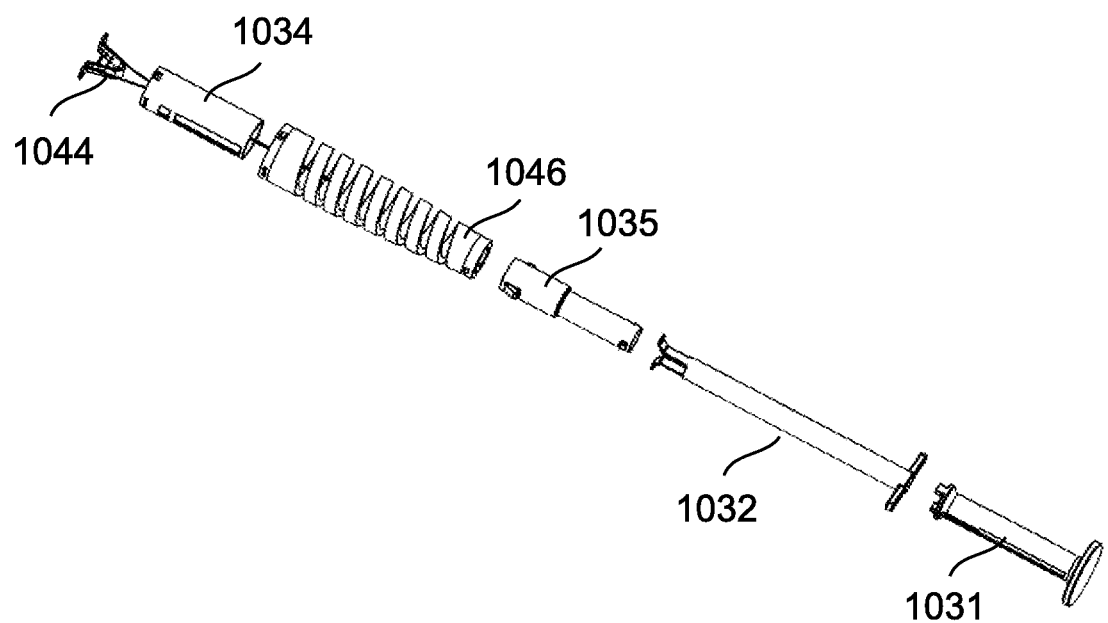
FIG. 11 is an exploded view of the ball-type prolapse treating device and the applicator of FIG. 10A, in accordance with an exemplary embodiment of the invention.

FIG. 11 is an exploded view of the ball-type prolapse treating device 1000 and the applicator 1030 of FIG. 10A, in accordance with an exemplary embodiment of the invention. In an embodiment of the invention, device 1000 is configured and operates similarly to device 700, with the outer bar tube 702 of device 700 replaced by spiral tube 1046, shown in FIG. 11, of device 1000.

Figures 12A, 12B:
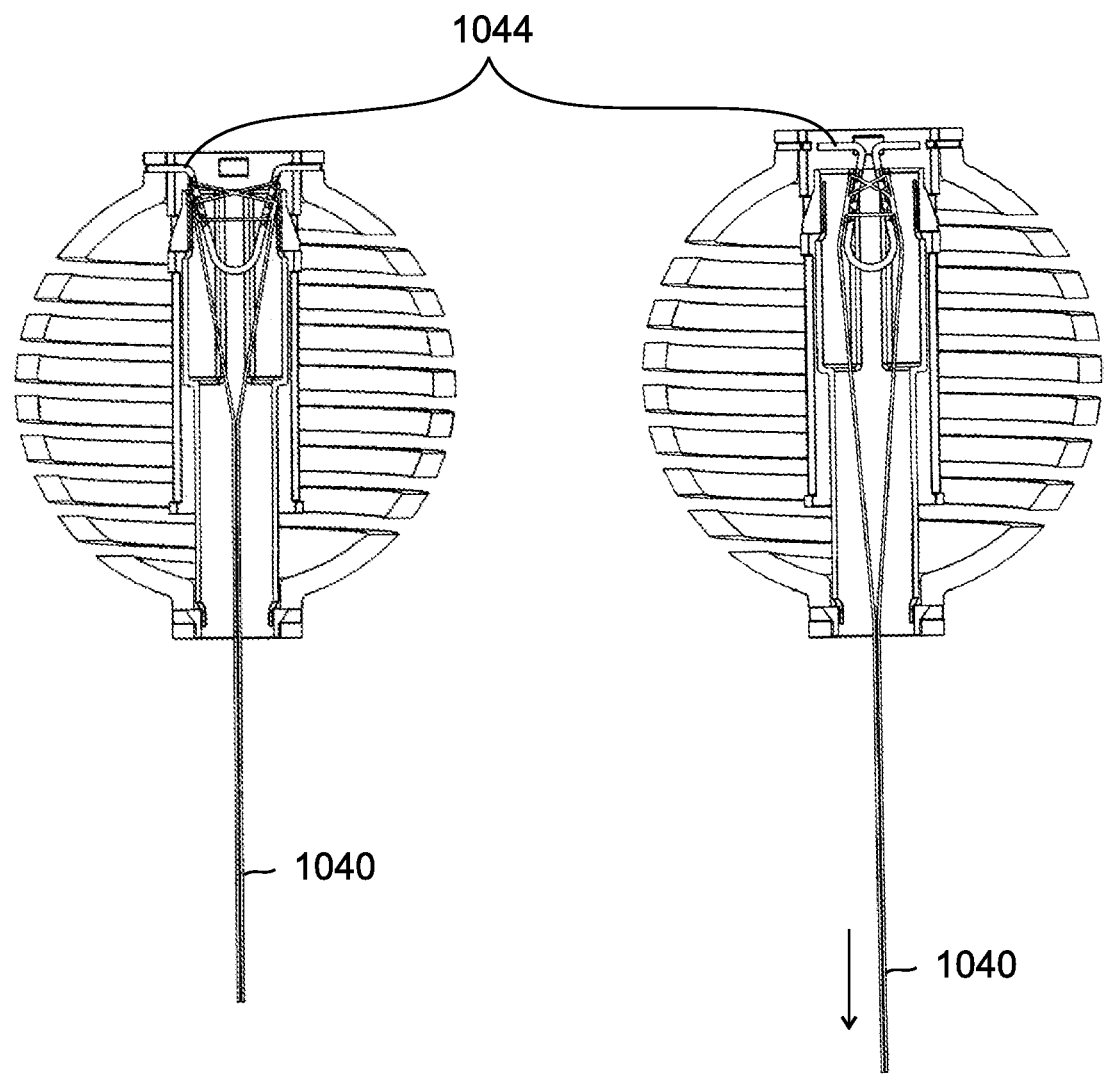
FIGS. 12A-12B are side views of the ball-type device of FIG. 10B showing a holding bar extended and retracted, respectively, in accordance with an exemplary embodiment of the invention.

FIGS. 12A-12B are side views of the ball-type device of FIG. 10B showing a holding bar 1044 extended and retracted, respectively, in accordance with an exemplary embodiment of the invention. To remove the device 1000 from the user's vagina, a removal string 1040 connected to the bar 1044 is pulled in a proximal direction, causing a deflection of the bar 1044, releasing the now-connected telescopic tubes 1034, 1035 from the spiral tube 1046 and converting the device 1000 from the expanded, ball state 120 to the collapsed state 110.

Figures 13A, 13B:
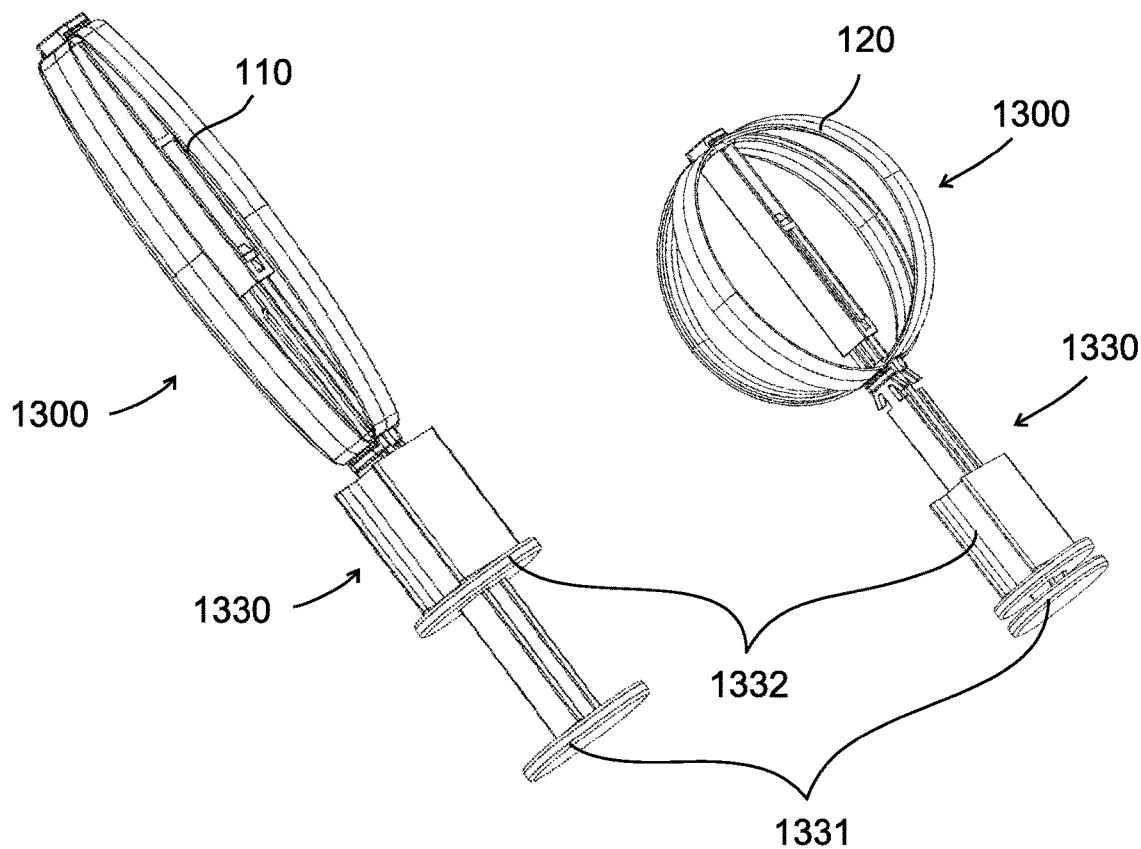
FIGS. 13A-13B are perspective closed and open, respectively, views of a ball-type prolapse treating device with opposing u-shaped elements attached to an applicator, in accordance with an exemplary embodiment of the invention.

FIGS. 13A-13B are perspective closed 110 and open 120, respectively, views of a ball-type prolapse treating device 1300 with opposing u-shaped elements 1302, 1304 attached to an applicator 1330, in accordance with an exemplary embodiment of the invention.

Figure 14:
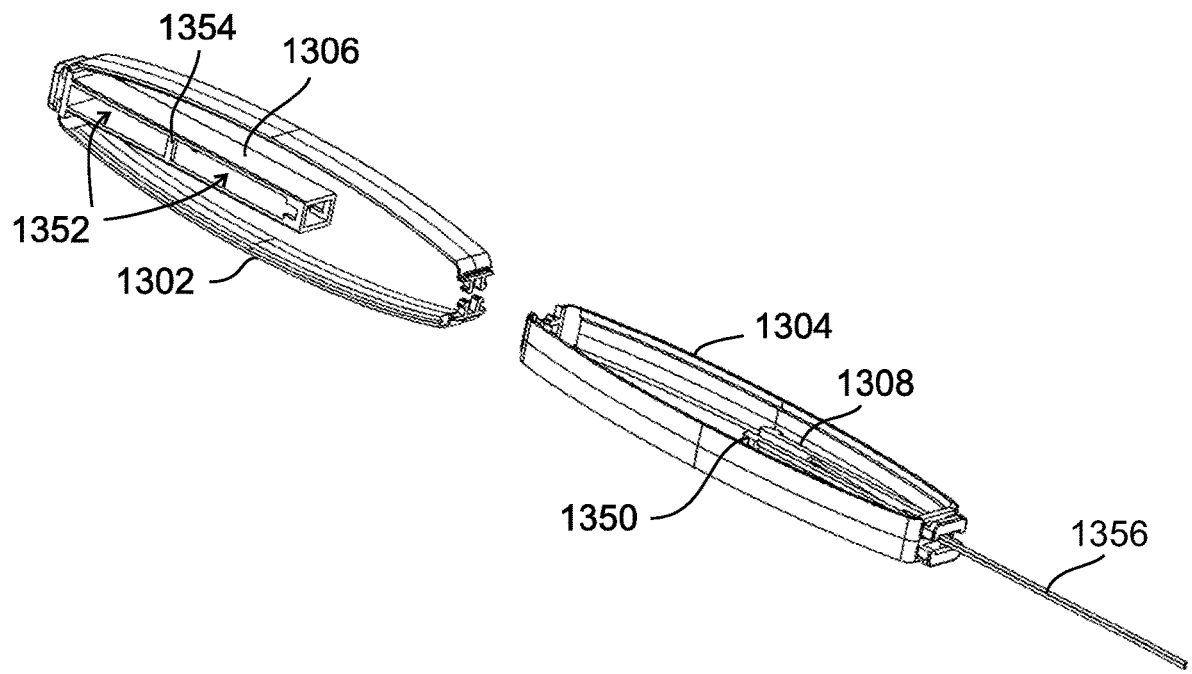
FIG. 14 is a perspective view of the ball-type prolapse treating device of FIG. 13A split apart, in accordance with an exemplary embodiment of the invention.

FIG. 14 is a perspective view of the ball-type prolapse treating device 1300 of FIG. 13A split apart into the two component elements 1302, 1304, in accordance with an exemplary embodiment of the invention. In an embodiment of the invention, the two elements 1302, 1304 are assembled concentrically opposing each other and orthogonal to each other. In an embodiment of the invention, the upper element 1302 is provided with an outer telescoping tube 1306 and the lower element 1304 is provided with a toothed, sliding post 1308. In an embodiment of the invention, the sliding post 1308 slides coaxially within the outer telescoping tube 1306 during device 1300 expansion. Teeth 1350 provided to the top or distal end of the sliding post 1308 are configured to travel within a slot 1352 in the outer telescoping tube 1306, whereby in a reversibly locked expanded state 120, the elastically deformable, biased teeth 1350 are pushed over a block 1354 and snap open, reversibly preventing the device 1300 from returning to the collapsed state 110.

In an embodiment of the invention, each of the "U" elements 1302, 1304 has an open base. However, by connecting them to each other, each of their respective bases are closed by the other element, forming two orthogonal closed frames (which are deformed into rings in the "expanded" state).

Removal of the device 1300 is achieved by pulling a removal string 1356 attached to the teeth 1350 in a proximal direction. The removal string 1356 is attached to the teeth 1350 in such a way (for example, by a connector 1358) as to cause the teeth to move towards a central major axis of the device 1300 and out of the slot 1352, allowing the teeth 1350 to move past the block 1354, releasing the outer telescoping tube 1306 and allowing the device 1300 to return to the collapsed state 110.

Figures 15A, 15B:
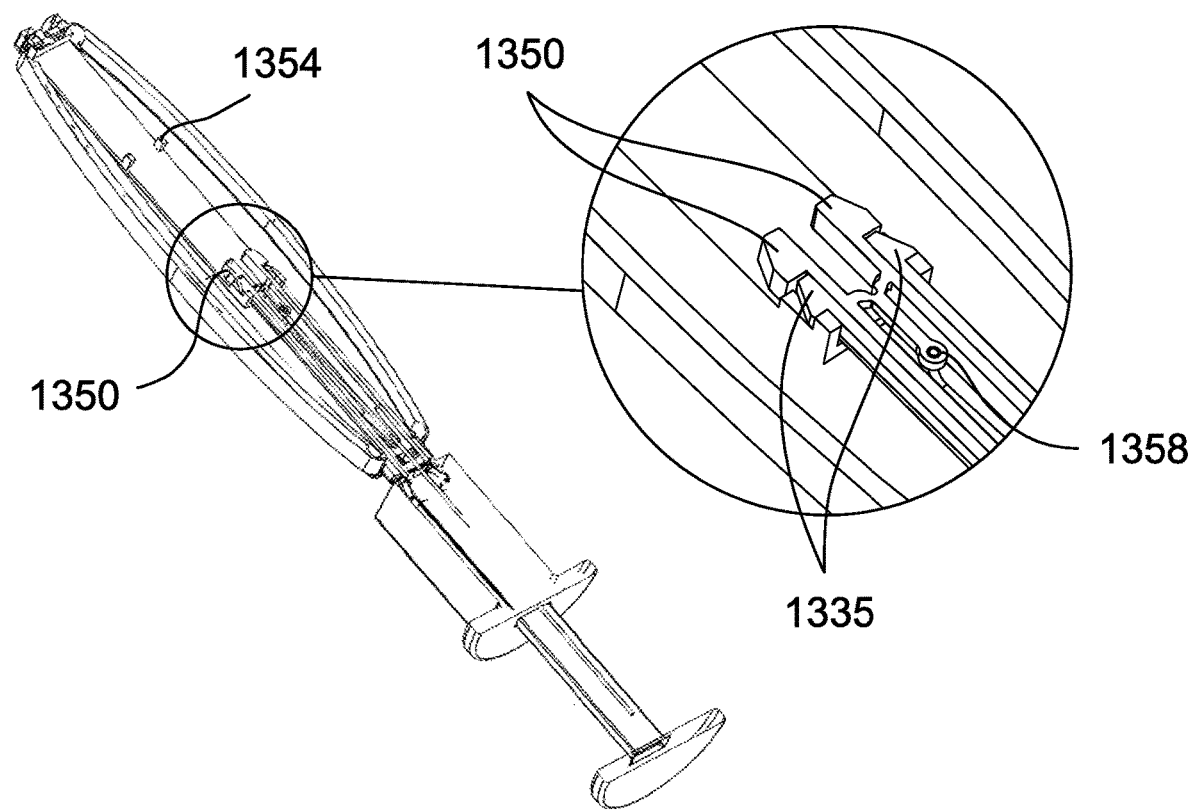
FIG. 15A is a cross-sectional view of the device of FIG. 13A, in accordance with an exemplary embodiment of the invention.
FIG. 15B is a close-up, cross-sectional view of a locking mechanism of the device of FIG. 13A, in accordance with an exemplary embodiment of the invention.

The applicator 1330 includes two components: a pessary holder 1331 and a puller 1332. FIG. 15A is a cross-sectional view of the device 1300 of FIG. 13A, in accordance with an exemplary embodiment of the invention. The puller 1332 is configured with snapping teeth 1335 that snap to the outer telescoping tube 1306, shown in FIG. 15B, a close-up, cross-sectional view of a locking mechanism of the device of FIG. 13A, in accordance with an exemplary embodiment of the invention. In an embodiment of the invention, the snapping teeth 1335 are reinforced/backed by the post 1308 preventing the snapping teeth 1335 from bending prematurely. The teeth 1335 are configured such that when the device 1300 attains the expanded state 120, the snapping teeth 1335 extend past the post 1308, bend inwards and release from the outer telescoping tube 1306. Then, the puller 1332 is removed together with the holder 1331 and the device 1300 is left inside the user's vagina.

Figure 16A:
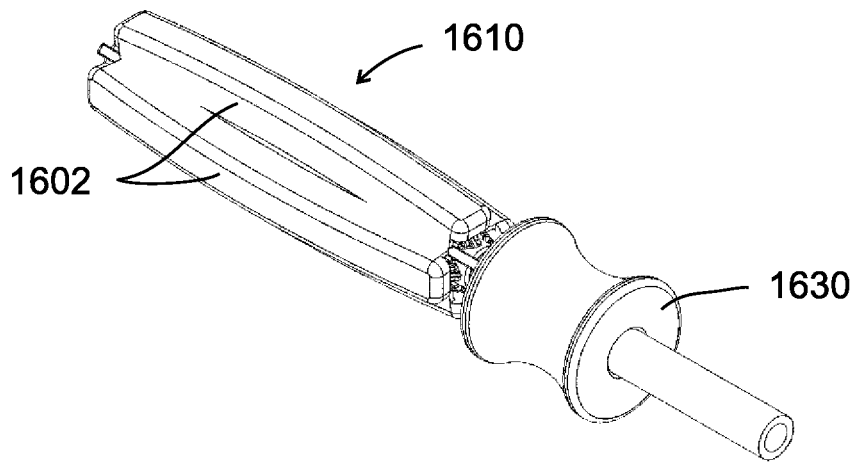
FIGS. 16A-16C are perspective views of a prolapse treating device in closed and opened states made of elastic arcs connected by coaxial telescopic elements, in accordance with an exemplary embodiment of the invention.

FIG. 16A is a perspective view of a prolapse treating device 1600 in its closed state 1610 made of three or more elastic arcs 1602 connected to two concentric telescopic elements. The device 1600 is attached to an applicator 1630, in accordance with an exemplary embodiment of the invention.

Figure 16B:
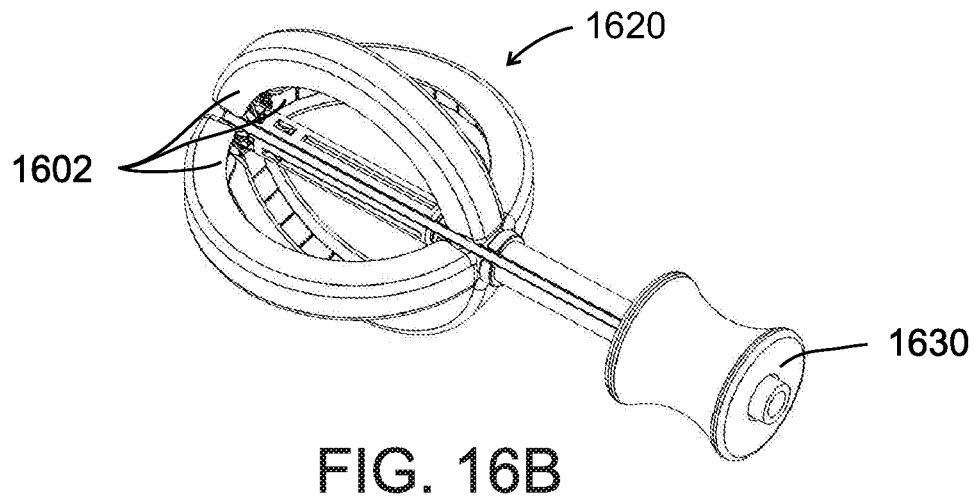
Figure 16C:
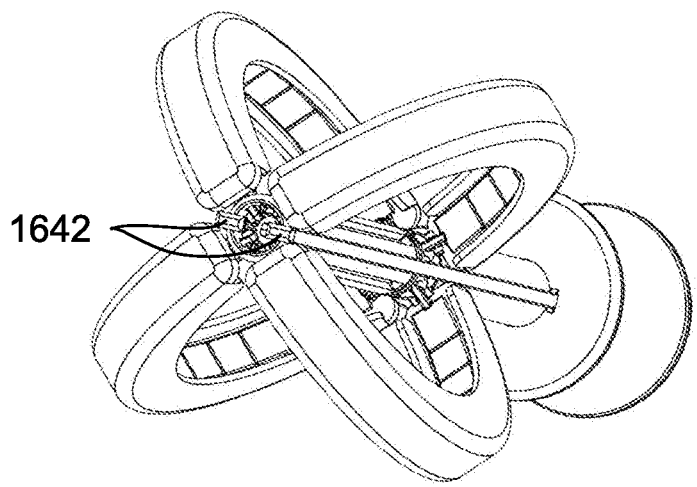

FIGS. 16B-16C are perspective views of the prolapse treating device 1600 of FIG. 16A in its opened state 1620.

Figure 17:
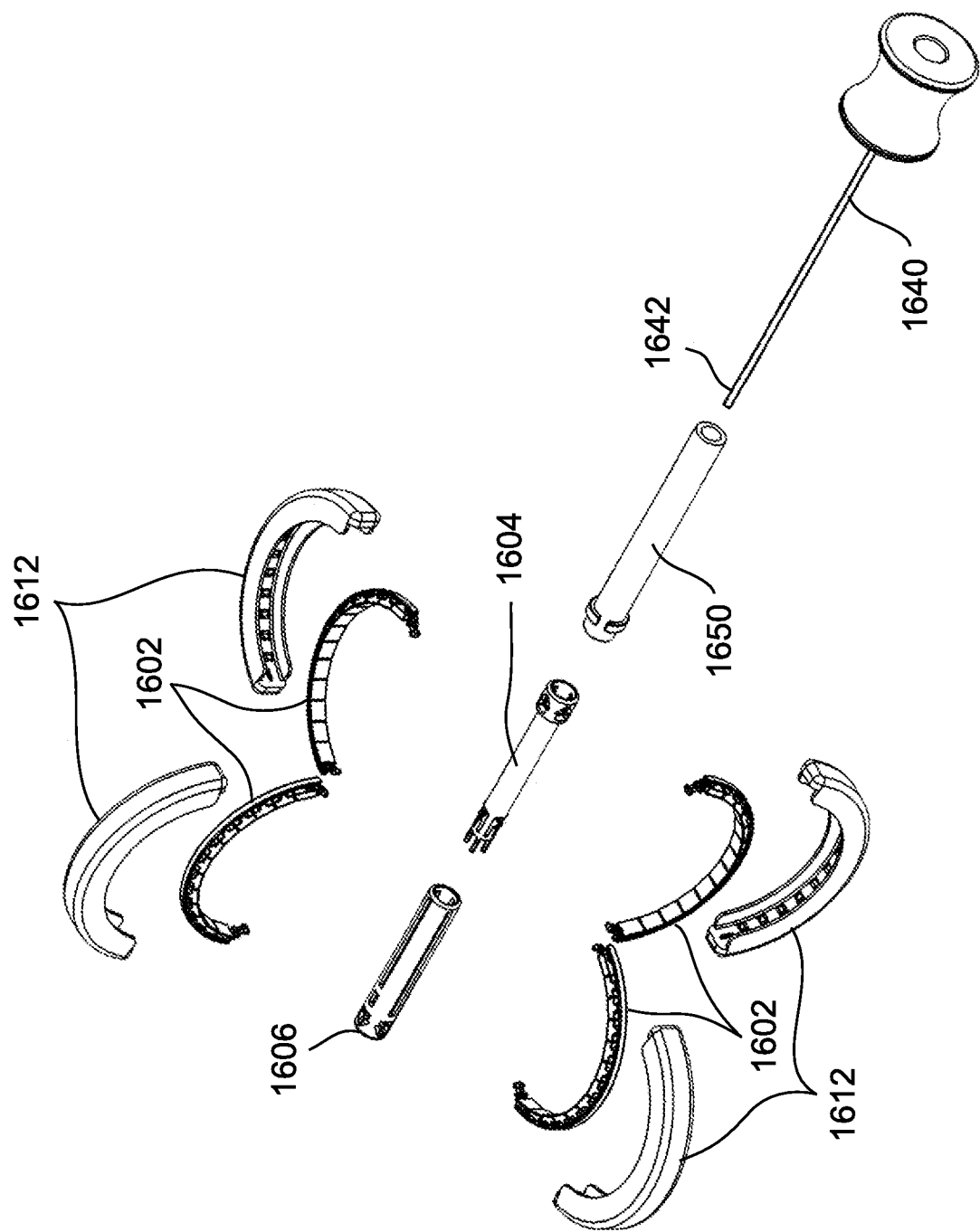
FIG. 17 is an exploded view of the prolapse treating device of FIG. 16A, in accordance with an exemplary embodiment of the invention.

FIG. 17 is an exploded view of the prolapse treating device and applicator of FIG. 16A showing the assembly relations between the device's components, in accordance with an exemplary embodiment of the invention. The elastic arcs elements 1602 are attached to the lower telescopic tube 1604 and to the upper telescopic tube 1606 by axis inserted through slots in the telescopic tube elements 1604, 1606. The lower telescopic tube 1604 has snapping teeth 1608 led by slots within the upper telescopic tube 1606. Each of the elastic arcs is covered by a padding cover 1612 to provide better force distribution of the device on vaginal walls.

Figure 18A:
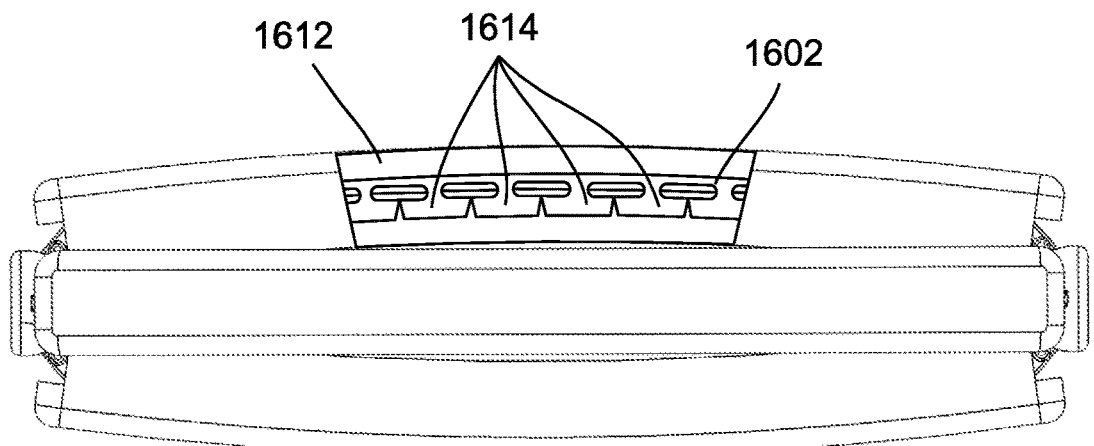
FIGS. 18A-18B are front views of the device of FIG. 16A, in accordance with an exemplary embodiment of the invention.
Figure 18B:
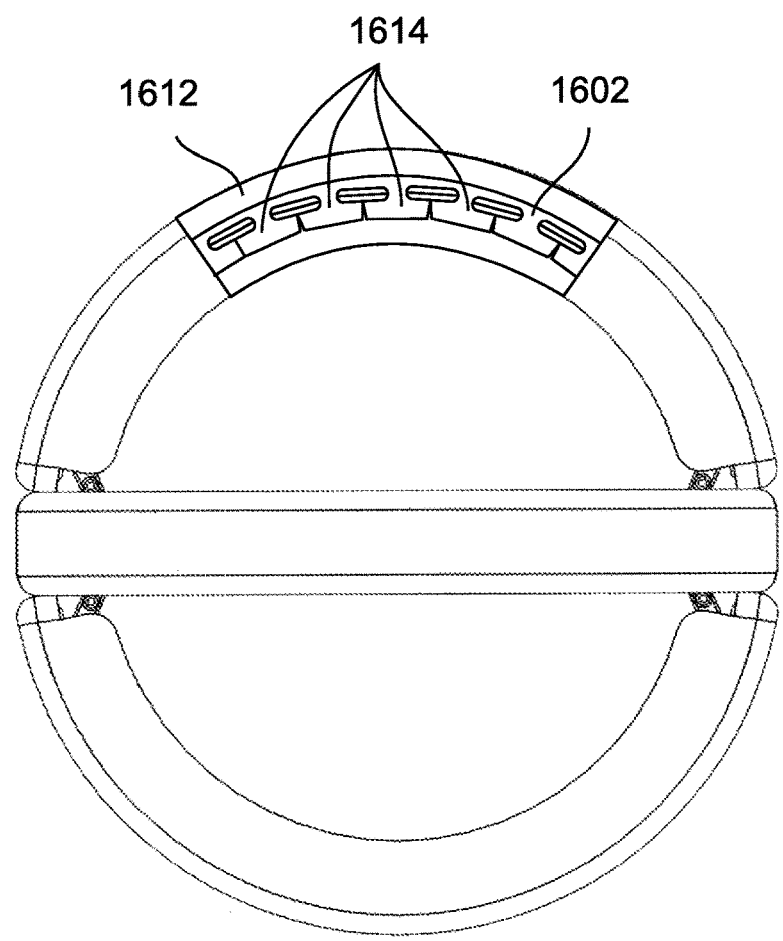

FIG. 18A is a front view of the device of FIG. 16A in its closed state 1610 having a broken out section revealing the elastic arc 1602 and FIG. 18B is a front view of the device in its opened state 1620 having a similar broken out section, in accordance with an exemplary embodiment of the invention. In an embodiment of the invention a plurality of blocks 1614 are connected to the internal side of each elastic arc 1602. When the telescopic tube elements are pressed towards each other the arcs 1602 are twisted to a smaller radius and the gaps between the blocks 1614 are closed. The telescopic tubes are locked by a locking mechanism (FIG. 19B) holding the device in the open state and the blocks in contact with each-other. The contact between the blocks elevates the rigidity of the device and allows it to keep its shape under the external pressure of the vagina.

FIG. 19A is a cross-sectional view of the device 1600 in its opened state, in accordance with an exemplary embodiment of the invention. The snapping teeth 1608 of the lower telescopic tube 1604 slides within slots in upper telescoping tube 1606 during device 1600 expansion until they encounter a "bridge" in the slot, climb and snap to it (FIG. 19B). The snap of the teeth is locking the device 1600 in its open state 1620 preventing it from returning to the collapsed state 1610.

Removal of the device 1600 is achieved by pulling a removal string 1616 attached to the snapping teeth 1608 in a proximal direction. The removal string 1616 is threaded in a hole in the snapping teeth 1608. When the removal string is pulled the snapping teeth move towards a central major axis of the device 1600 and released from the "bridge" in the slot of the upper telescopic tube 1606, releasing the upper telescoping tube and allowing the device 1600 to return to the collapsed state 1610.

The applicator 1630 includes two components: a pessary holder 1640 and a pusher 1650. The holder 1640 is configured with snapping teeth 1642 that snap to the rim of the upper telescoping tube 1606, shown in FIG. 16C. The lower telescopic tube 1604 has forward protruding pegs 1618. When the device reaches its expanded state 1620, the pegs 1618 come in contact with the holder snapping teeth 1642, push them over the upper telescopic tube rim, allowing the snapping teeth to bend outwards and release the upper telescopic tube 1606. Then, the holder 1640 is removed together with the pusher 1650 and the device 1600 is left inside the user's vagina.

Figure 20A:
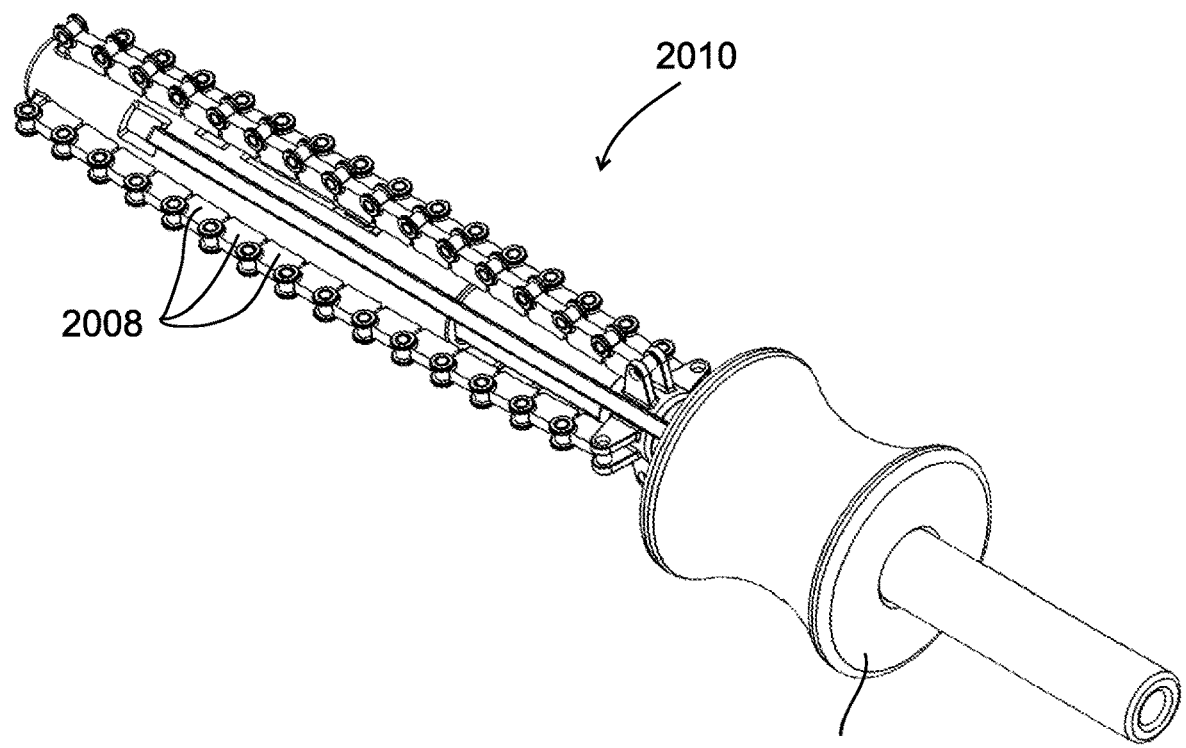
FIGS. 20A-20B are perspective closed and open, respectively, views of a prolapse treating device made of coaxial telescopic elements and a plurality of block elements, in accordance with an exemplary embodiment of the invention.
Figure 20B:
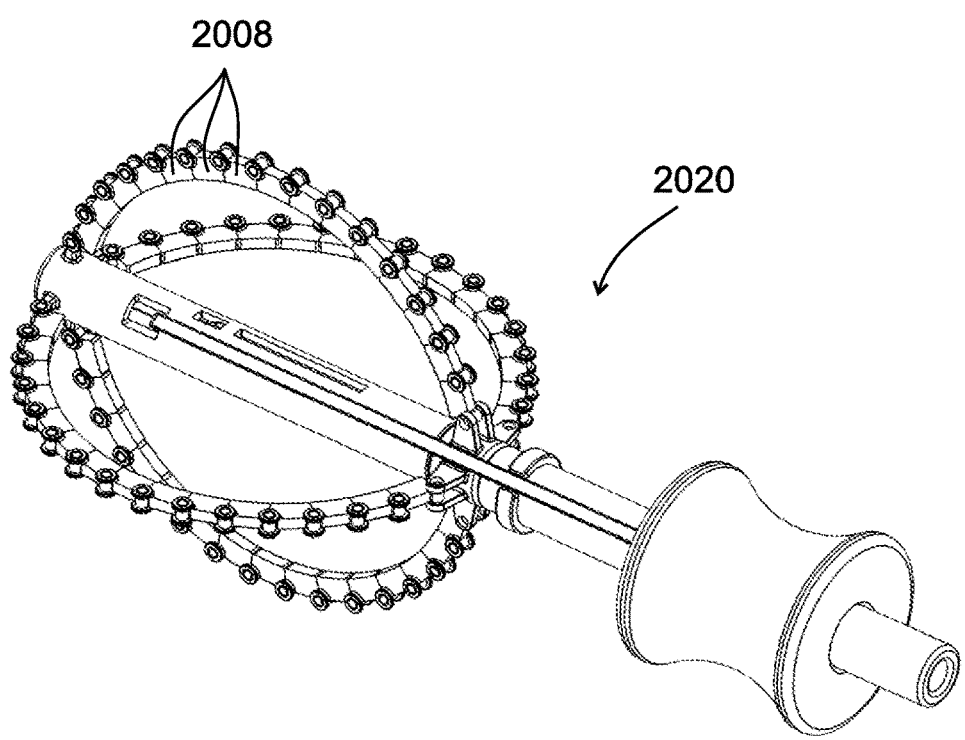

FIGS. 20A-20B are perspective closed 2010 and open 2020, respectively, views of a prolapse treating device 2000 made of coaxial telescopic elements and a plurality of block elements 2008 attached to an applicator 2030, in accordance with an exemplary embodiment of the invention.

Figure 21:
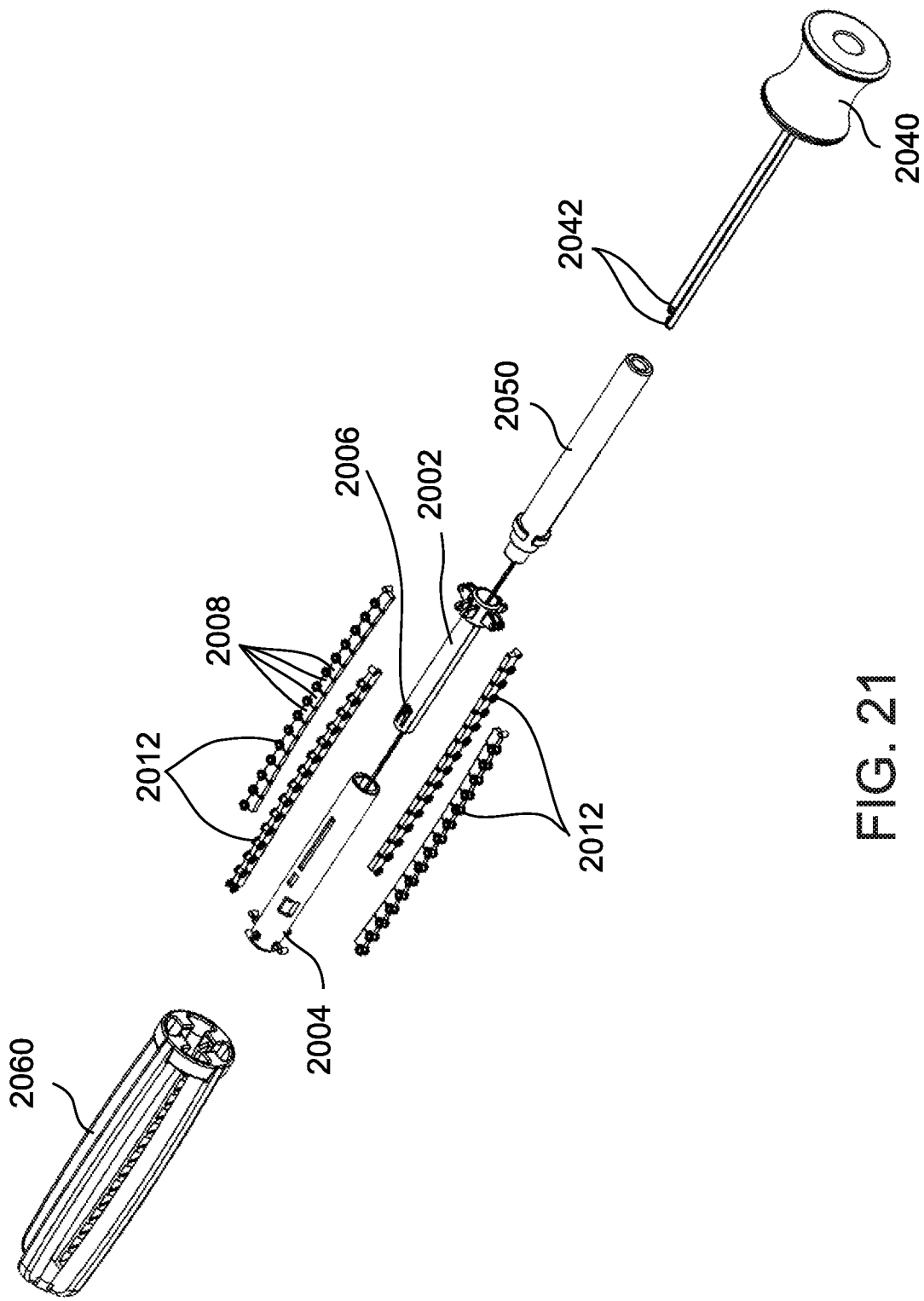
FIG. 21 is an exploded view of the prolapse treating device of FIG. 20A, in accordance with an exemplary embodiment of the invention.

FIG. 21 is an exploded view of the prolapse treating device showing the assembly relations between the device's components, in accordance with an exemplary embodiment of the invention. Block elements 2008 are connected to each other by integral hinges to form a chain 2012. Each of several chains (3 or more) is connected (by hinges) to a lower telescopic tube 2002 on one of it ends and to an upper telescopic tube 2004 on its other end. The lower telescopic tube 2002 has snapping teeth 2006 led by slots within the upper telescopic tube 2004.

FIG. 22 is a front view of a chain 2012 made of a plurality of block elements 2008.

When the lower telescopic tube 2002 and the upper telescopic tube 2004 are pressed towards each other the block elements 2008 are rotated around their hinges until they come to full contact with each-other. When the block elements are in full contact with each other, the chains have a small radius arc shape and device reaches its open state 2020. The telescopic tubes are locked by a locking mechanism (FIG. 23B) holding the ring elements in the open state and the blocks in full contact with each-other. The contact between the blocks elevates the rigidity of the device and allows it to keep its shape under the external pressure of the vagina.

A padding cover 2060 is placed over the ring elements to provide better force distribution of the device on vaginal walls.

FIG. 23A is a cross-sectional view of the device 2000 of FIG. 20A, in accordance with an exemplary embodiment of the invention. The snapping teeth 2006 of the lower telescopic tube 2002 slide within slots in upper telescoping tube 2004 during device 2000 expansion until they encounter a "bridge" in the slot, climb and snap to it (FIG. 23B). The snap of the teeth is locking the device 2000 in its open state 2020 preventing it from returning to the collapsed state 2010.

Removal of the device 2000 is achieved by pulling a removal string 2016 attached to the snapping teeth 2006 in a proximal direction. The removal string 2016 movement deforms the snapping teeth towards a central major axis of the device 2000 and out of the slot in the upper telescopic tube 2004, releasing the upper telescoping tube and allowing the device 2000 to return to the collapsed state 2010.

The applicator 2030 includes two components: a pessary holder 2040 and a pusher 2050. The holder 2040 is configured with snapping teeth 2042 that snap to the upper telescoping tube 2004. In an embodiment of the invention, when the device reaches its expanded state 2020, the lower telescopic tube snapping teeth 2006 push the holder snapping teeth 2042 upwards causing them to bend outwards and release from the upper telescopic tube 2004. Then, the holder 2040 is removed together with the pusher 2050 and the device 2000 is left inside the user's vagina.

Figure 24A:
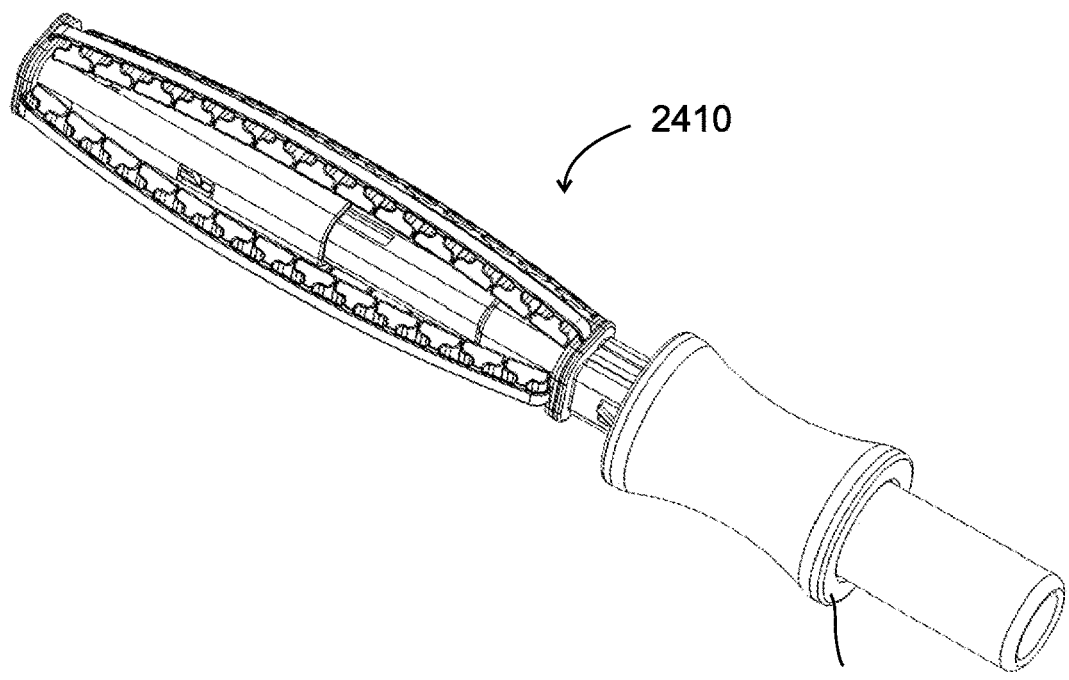
FIGS. 24A-24B are perspective views of a prolapse treating device in closed and opened states made of two orthogonal ring elements joined in their bases (upper and lower) by coaxial telescopic elements, in accordance with an exemplary embodiment of the invention.
Figure 24B:
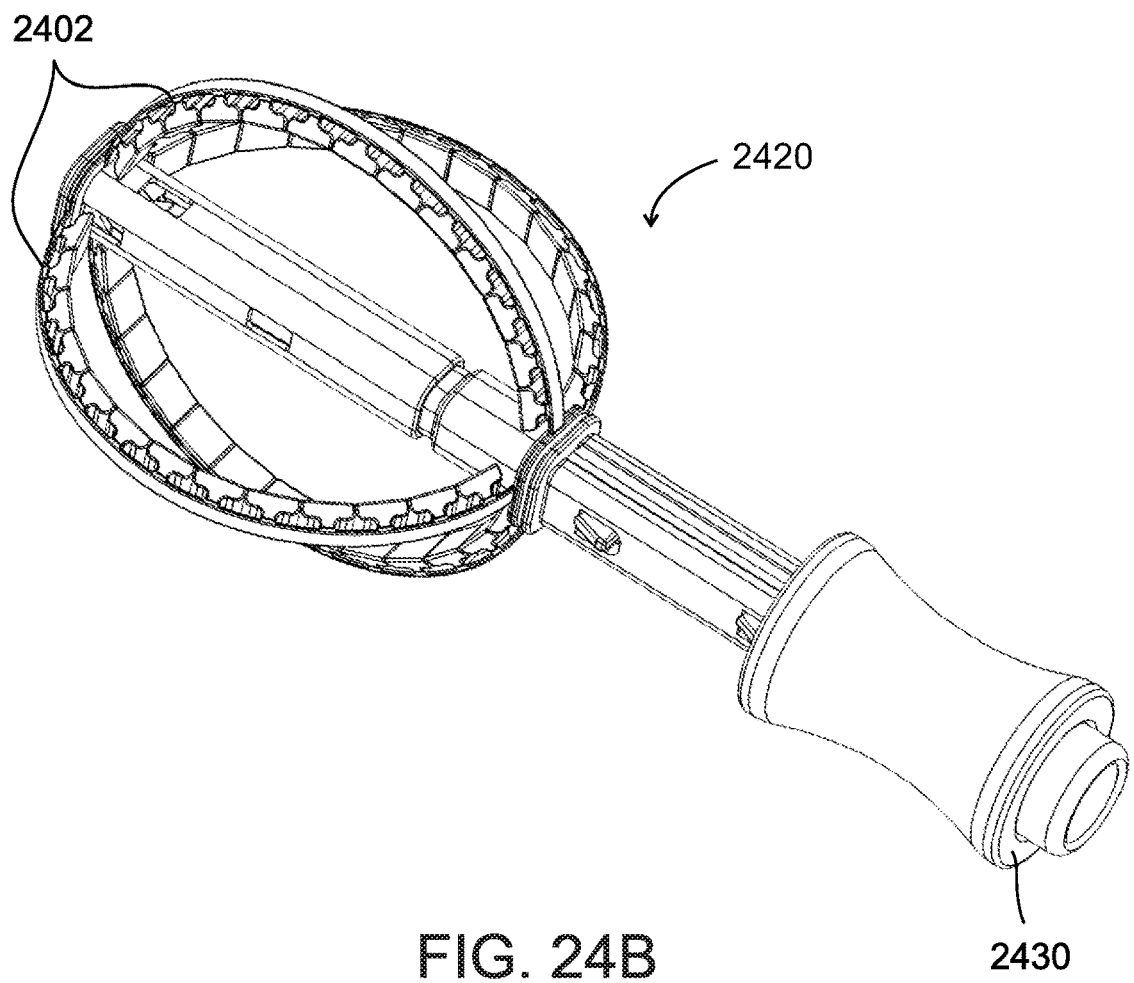

FIGS. 24A-24B are perspective views of a prolapse treating device 2400 in closed state 2410 and open state 2420, respectively, made of two orthogonal ring elements 2402 attached to an applicator 2430, in accordance with an exemplary embodiment of the invention.

Figure 25:
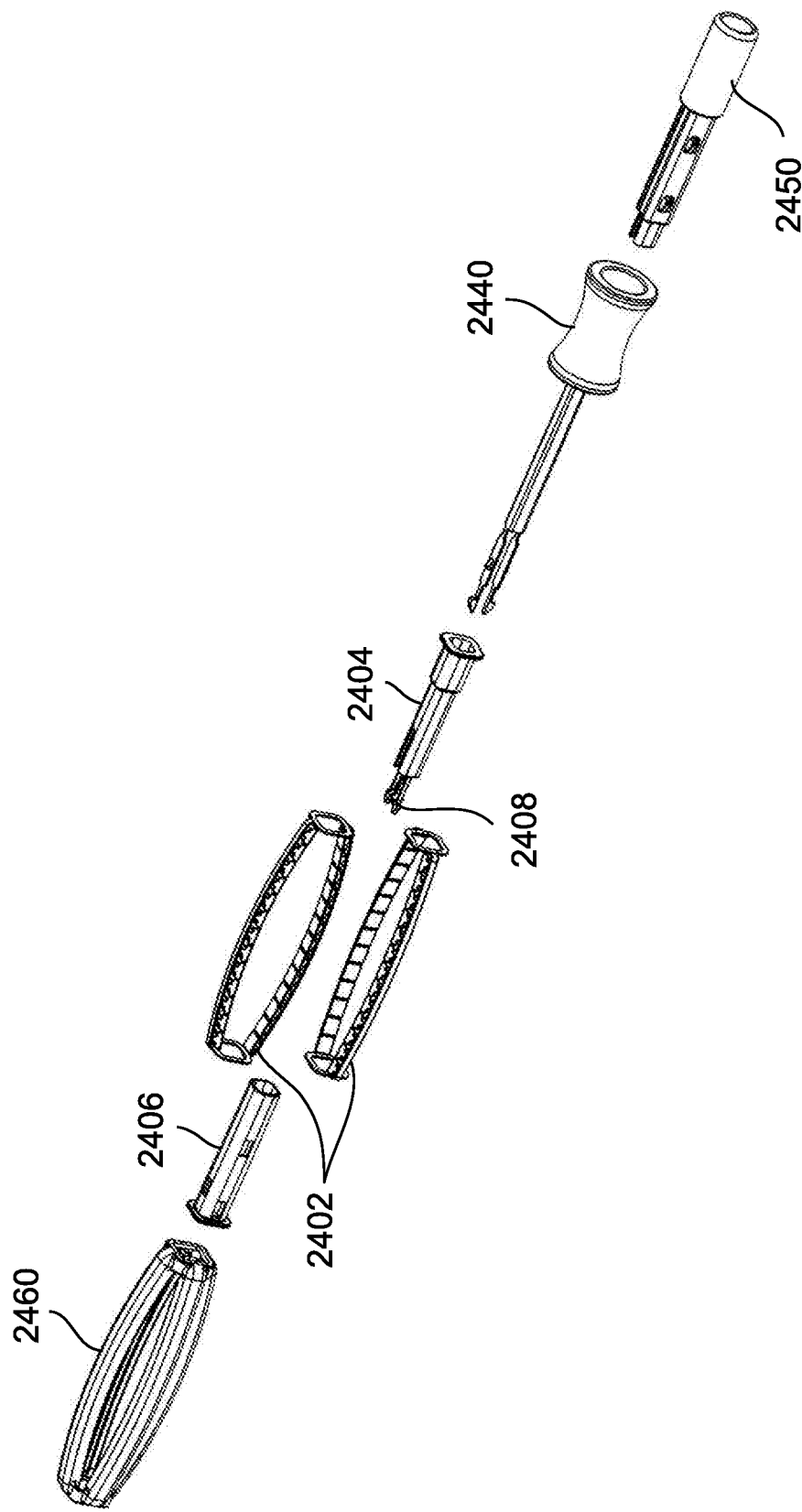
FIG. 25 is an exploded view of the ball-type prolapse treating device of FIG. 24A, in accordance with an exemplary embodiment of the invention.

FIG. 25 is an exploded view of the prolapse treating device showing the assembly relations between the device's components, in accordance with an exemplary embodiment of the invention. The two ring elements 2402 are placed orthogonally and coaxially to each other and the lower telescopic tube 2404 and upper telescopic tube 2406 are inserted within holes in the ring elements bases to hold both ring elements. The lower telescopic tube 2404 has snapping teeth 2408 led by slots within the upper telescopic tube 2406. A padding cover 2460 is placed over the ring elements to provide better force distribution of the device on vaginal walls.

Figure 26A:
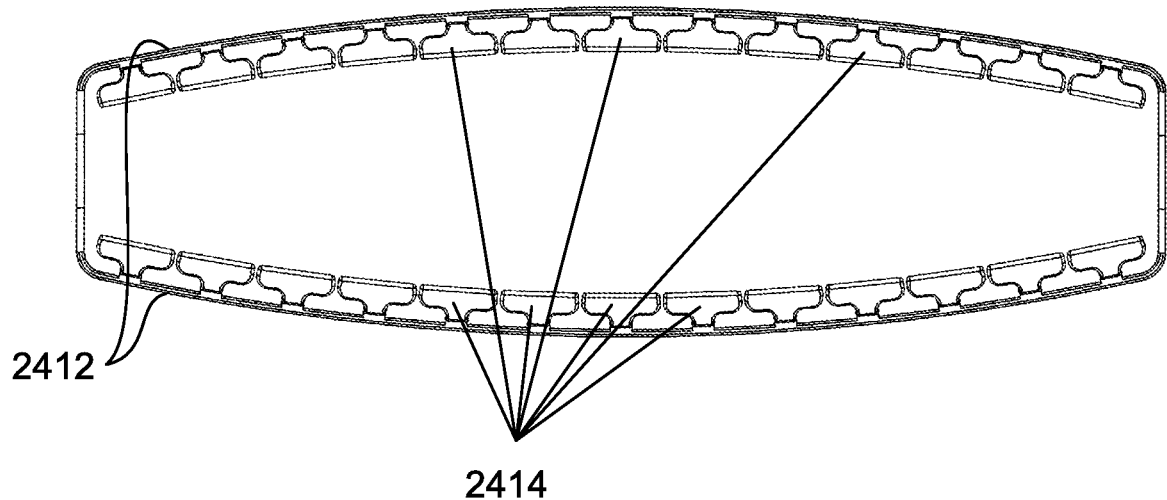
FIGS. 26A-26B are front views of one of the ring elements in closed and opened states, in accordance with an exemplary embodiment of the invention.
Figure 26B:
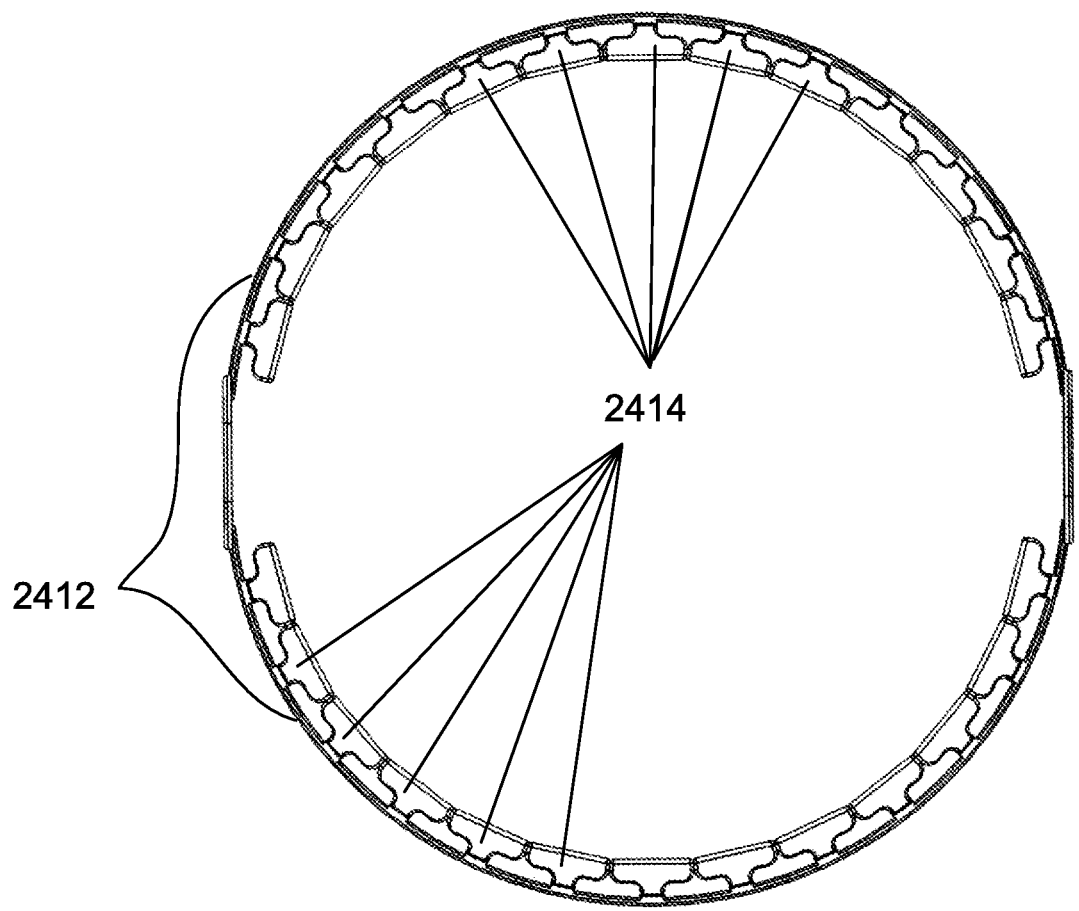

FIGS. 26A-26B are a front views of a ring element 2402, in closed state and opened state, respectively, in accordance with an exemplary embodiment of the invention. In an embodiment of the invention, the ring element 2402 has two opposing arcs 2412. A plurality of blocks 2414 are connected to the internal side of the arcs. When the two bases of the ring elements are pressed towards each other the arcs 2412 are twisted to a smaller radius and the gaps between the blocks 2414 are closed. The telescopic tubes are locked by a locking mechanism (FIG. 27B) holding the ring elements in the opened state 2420 and the blocks in contact with each-other. The contact between the blocks elevates the rigidity of the device and allows it to keep its shape under the external pressure of the vagina.

FIG. 27A is a cross-sectional view of the device 2400 of FIG. 24A, in accordance with an exemplary embodiment of the invention. The snapping teeth 2408 of the lower telescopic tube 2404 slides within the upper telescoping tube 2406 during device 2400 expansion until they encounter a locking slot, bend outwards and snap to it (FIG. 27B). The snap of the teeth is locking the device 2400 in its opened state 2420 preventing it from returning to the closed state 2410.

Removal of the device 2400 is achieved by pulling a removal string 2416 attached to the snapping teeth 2408 in a proximal direction. The removal string 2416 is attached to a "V" shaped bridge connecting the snapping teeth 2408. When the removal string is pulled the "V" shaped bridge is twisted causing the snapping teeth to move towards a central major axis of the device 2400 and out of the slot in the upper telescopic tube 2406, releasing the upper telescoping tube and allowing the device 2400 to return to the collapsed state 2410 (FIGS. 28A-28B).

Figure 29A:
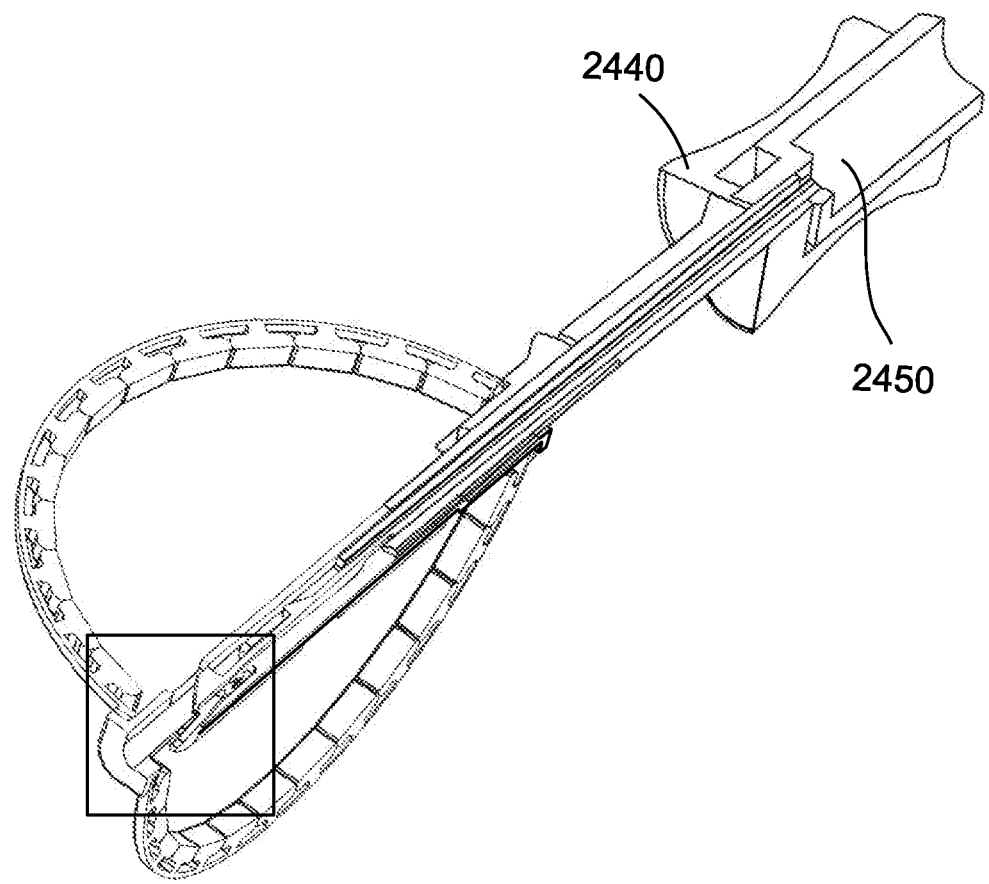
FIG. 29A is a perspective cross-sectional view of device of FIG. 24A and its applicator, in accordance with an exemplary embodiment of the invention.
Figures 29B, 29C:
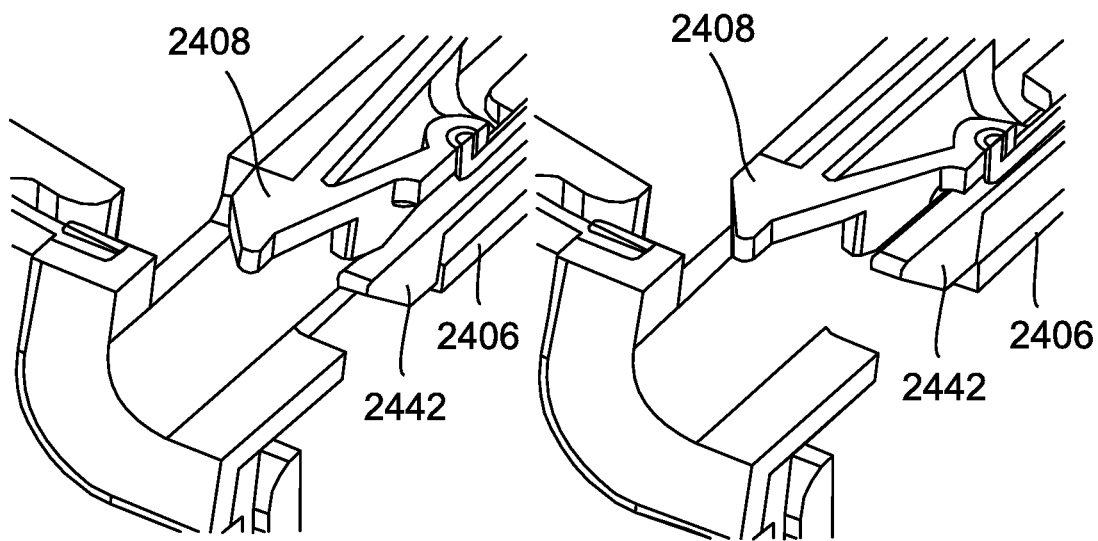
FIGS. 29B-29C are close up views of FIG. 29A.

FIG. 29A is a perspective cross-sectional view of device 2400 of FIG. 24A, in accordance with an exemplary embodiment of the invention. The applicator 2430 includes two components: a holder 2440 and a pusher 2450. The holder 2440 is configured with snapping teeth 2442 that snap to the upper telescoping tube 2406, FIG. 29B is a close-up view of a locking mechanism of the device of FIG. 24A and the applicator holder snapping teeth. In an embodiment of the invention, the holder snapping teeth 2442 are backed by the "V" shaped bridge of the lower telescopic tube preventing the holder snapping teeth 2442 from bending prematurely. When the device reaches its expanded state 2420, the lower telescopic tube snapping teeth 2408 are released outwards, twisting the "V" shaped bridge in a way that allows the bend inwards and release of the holder snapping teeth from the upper telescopic tube 2406 (FIG. 29C). Then, the holder 2440 is removed together with the pusher 2450 and the device 2400 is left inside the user's vagina.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference.

In addition, citation or identification of any reference in this application shall not be construed as an admission that such reference is available as prior art to the present invention. To the extent that section headings are used, they should not be construed as necessarily limiting.

What is claimed is:

1. A device sized and shaped for alleviating pelvic organ prolapse when inserted into a vagina, comprising:
a treatment rendering portion configured to be adjustable between a first, collapsed state and a second, expanded state, where the second expanded state extends substantially in three dimensions,
where the treatment rendering portion comprises three or more plastic arcs, each having a distal end and a proximal end, connected to two concentric telescopic elements,
where the distal ends of the three or more plastic arcs do not intersect directly with each other;
wherein the concentric telescopic elements are an external tube and an internal tube coaxial with and slidable within the external tube, the internal tube and the external tube releasably interlockable to prevent sliding when in the expanded state, where the external tube is configured with a slot within which at least one locking pin of the internal tube is received to interlock the external and internal tubes; and,
wherein the device further comprises a removal device comprising a string and a removal disk attached to the string for converting the device from the second, expanded state to the first, collapsed state, and wherein the removal disk is configured to directly collapse on the at least one locking pin when the string is pulled in a proximal direction, thereby pressing the at least one locking pin towards a central axis of the device, for unlocking the device.

2. A device according to claim 1, where the three or more plastic arcs of the treatment rendering portion comprise a plurality of bendable arcs.

3. A device according to claim 2, where distal ends of the bendable arcs are connected to the external tube and proximal ends of the bendable arcs are connected to the internal tube.

4. A device according to claim 2, where proximal ends of the bendable arcs are integral with the internal tube, and distal ends of the bendable arcs are connected to the external tube.

5. A device according to claim 1, where the treatment rendering portion is an outer bar tube with a distal end connected to an upper tube and with a proximal end connected to a lower tube, where the lower tube is coaxial and slidable within the upper tube and where the upper and lower tubes are coaxial and internal to the outer bar tube.

6. A device according to claim 5, where the upper tube and the lower tube releasably interlock to prevent sliding when in the expanded state.

7. A device according to claim 6, where the upper tube is configured with a slot within which at least one locking pin of the lower tube is received to interlock the upper and lower tubes.

8. A device according to claim 1, where the treatment rendering portion comprises an upper element and a lower element, where these elements are positioned concentrically opposing and orthogonal to each other.

9. A device according to claim 8, where the upper element is provided with an outer telescoping tube and the lower element is provided with a toothed, sliding post, where the sliding post slides coaxially within the outer telescoping tube during device expansion into the second, expanded state.

10. A device according to claim 9, where at least one tooth is provided to a distal end of the sliding post and where the tooth is configured to reversibly lock the device into the second, expanded state when the at least one tooth moves past a block provided in a slot in the outer telescoping tube.

11. A device according to claim 1, where the treatment rendering portion is rotationally symmetric.

12. A device according to claim 1, further comprising a locking mechanism.

13. A device according to claim 1, where the removal device further comprises a holding bar.

14. A system for alleviating pelvic organ prolapse when inserted into a vagina, comprising:
   (a) a device according to claim 1; and,
   (b) an applicator.

15. A system according to claim 14, where the applicator comprises a holder and a puller.

* * * * *